US011622455B2

(12) United States Patent
Seo et al.

(10) Patent No.: US 11,622,455 B2
(45) Date of Patent: Apr. 4, 2023

(54) WEARABLE ELECTRONIC DEVICE

(71) Applicant: Samsung Electronics Co., Ltd., Suwon-si (KR)

(72) Inventors: Ho-Seong Seo, Suwon-si (KR); Wataru Kaihotsu, Gunpo-si (KR); Yong-Woon Han, Gunpo-si (KR); Dong-Churl Kim, Ansan-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 581 days.

(21) Appl. No.: 16/690,787

(22) Filed: Nov. 21, 2019

(65) Prior Publication Data
US 2020/0093015 A1 Mar. 19, 2020

Related U.S. Application Data

(63) Continuation of application No. 14/816,535, filed on Aug. 3, 2015, now Pat. No. 10,517,182.

(30) Foreign Application Priority Data

Oct. 28, 2014 (KR) .......................... 10-2014-0147587

(51) Int. Cl.
*A61B 5/00* (2006.01)
*A61B 5/0205* (2006.01)
(Continued)

(52) U.S. Cl.
CPC ............. *H05K 5/0217* (2013.01); *A44C 5/04* (2013.01); *A61B 5/0022* (2013.01); *A61B 5/01* (2013.01);
(Continued)

(58) Field of Classification Search
CPC ....... A61B 5/6824; A61B 5/681; A61B 5/021; A61B 5/6843; A61B 5/6831;
(Continued)

(56) References Cited

U.S. PATENT DOCUMENTS 2,759,325 A 8/1956 Pinson
3,490,227 A 1/1970 Leonard
(Continued)

FOREIGN PATENT DOCUMENTS

CN 103393411 A 11/2013
CN 103561606 A 2/2014
(Continued)

OTHER PUBLICATIONS

Chinese Office Action dated Dec. 24, 2019, issued in Chinese Patent Application No. 104134273.
(Continued)

*Primary Examiner* — John R Downey
(74) *Attorney, Agent, or Firm* — Jefferson IP Law, LLP

(57) ABSTRACT

A wearable electronic device is provided. The wearable electronic device includes a main body and a wearing unit that allows the main body to be worn on a user's body. The wearing unit may include a first wearing member extending from the main body, a binding member coupled to the first wearing member to be moved in a longitudinal direction of the first wearing member, and a driving member installed in the first wearing member to move the binding member.

19 Claims, 19 Drawing Sheets

(51) Int. Cl.
*H05K 5/02* (2006.01)
*H05K 5/00* (2006.01)
*A61B 5/01* (2006.01)
*A61B 5/026* (2006.01)
*A44C 5/04* (2006.01)
*G06F 1/16* (2006.01)
*A61B 5/318* (2021.01)

(52) U.S. Cl.
CPC .......... *A61B 5/026* (2013.01); *A61B 5/02055* (2013.01); *A61B 5/318* (2021.01); *A61B 5/4806* (2013.01); *A61B 5/681* (2013.01); *G06F 1/163* (2013.01); *H05K 5/0086* (2013.01); *H05K 5/0221* (2013.01)

(58) Field of Classification Search
CPC . A61B 5/1123; A61B 5/1118; A61B 5/02438; A61B 5/0002; A61B 5/02055
USPC ....... 600/300, 301, 479, 483, 485, 490, 499, 600/500, 503, 508
See application file for complete search history.

(56) References Cited

U.S. PATENT DOCUMENTS

| | | | |
|---|---|---|---|
| 4,819,860 A * | 4/1989 | Hargrove | A61B 5/681 128/903 |
| 5,485,848 A | 1/1996 | Jackson et al. | |
| 6,811,535 B2 | 11/2004 | Palti et al. | |
| 8,652,058 B2 | 2/2014 | Kim et al. | |
| 2002/0103423 A1 | 8/2002 | Chin et al. | |
| 2002/0109600 A1 | 8/2002 | Mault et al. | |
| 2003/0083083 A1 | 5/2003 | Marmaropoulos et al. | |
| 2003/0107487 A1 | 6/2003 | Korman et al. | |
| 2005/0075542 A1 * | 4/2005 | Goldreich | G16H 40/67 600/300 |
| 2005/0234312 A1 | 10/2005 | Suzuki et al. | |
| 2006/0074362 A1 | 4/2006 | Rousso et al. | |
| 2009/0322513 A1 * | 12/2009 | Hwang | H04W 4/90 600/301 |
| 2010/0268092 A1 | 10/2010 | Kobayashi et al. | |
| 2010/0309000 A1 | 12/2010 | Munthe-Kaas et al. | |
| 2010/0324384 A1 | 12/2010 | Moon et al. | |
| 2011/0021932 A1 | 1/2011 | Kim et al. | |
| 2011/0109329 A1 | 5/2011 | Diebold et al. | |
| 2012/0209532 A1 * | 8/2012 | Liang | G16H 20/30 702/19 |
| 2013/0261405 A1 * | 10/2013 | Lee | A61B 5/14542 600/509 |
| 2014/0018686 A1 | 1/2014 | Medelius et al. | |
| 2014/0053602 A1 | 2/2014 | Catheline et al. | |
| 2014/0078871 A1 | 3/2014 | Savoy | |
| 2014/0142403 A1 | 5/2014 | Brumback et al. | |
| 2014/0176422 A1 | 6/2014 | Brumback et al. | |
| 2014/0194793 A1 * | 7/2014 | Nakata | G01S 13/87 601/48 |
| 2014/0213920 A1 * | 7/2014 | Lee | A61B 5/222 600/509 |
| 2014/0221854 A1 * | 8/2014 | Wai | A61B 5/02444 600/508 |
| 2014/0221855 A1 | 8/2014 | McCaffrey | |
| 2014/0268522 A1 | 9/2014 | Tanaka et al. | |
| 2014/0278229 A1 * | 9/2014 | Hong | A61B 5/02433 702/160 |
| 2014/0323840 A1 | 10/2014 | Ouwerkerk | |
| 2015/0091711 A1 * | 4/2015 | Kosonen | H04M 3/02 340/407.1 |
| 2015/0338979 A1 * | 11/2015 | Rhee | G06F 1/163 345/174 |
| 2015/0345985 A1 * | 12/2015 | Fung | A61B 5/1118 702/160 |
| 2017/0119314 A1 * | 5/2017 | Just | A61B 5/1118 |

FOREIGN PATENT DOCUMENTS

| | | |
|---|---|---|
| CN | 104042193 A | 9/2014 |
| CN | 104055492 A | 9/2014 |
| EP | 0 459 239 A2 | 12/1991 |
| EP | 1 609 413 A1 | 12/2005 |
| EP | 1 859 735 A1 | 11/2007 |
| EP | 2 770 454 A1 | 8/2014 |
| GB | 00977 A A.D. 1911 | 7/1911 |
| JP | H05-329117 A | 12/1993 |
| JP | 2001-276001 A | 10/2001 |
| JP | 2002-48053 A | 2/2002 |
| JP | 2004-147263 A | 5/2004 |
| JP | 2006-204401 A | 8/2006 |
| JP | 2007-125246 A | 5/2007 |
| JP | 2008-087110 A | 4/2008 |
| JP | 2008-279061 A | 11/2008 |
| JP | 2010-110634 A | 5/2010 |
| JP | 2010-220949 A | 10/2010 |
| KR | 10-2009-0099147 A | 9/2009 |
| KR | 10-2013-0111713 A | 10/2013 |
| WO | 2006/006158 A1 | 1/2006 |
| WO | 2006/018833 A2 | 2/2006 |
| WO | 2008/029399 A2 | 3/2008 |
| WO | 2008/087870 A1 | 7/2008 |
| WO | 2011/109716 A2 | 9/2011 |
| WO | 2011/163576 A1 | 12/2011 |
| WO | 2012/092221 A1 | 7/2012 |
| WO | 2012/135325 A2 | 10/2012 |
| WO | 2013/080075 A1 | 6/2013 |

OTHER PUBLICATIONS

Extended European Search Report dated Jul. 17, 2020, issued in European Patent Application No. 19210602.9.
Korean Office Action dated Mar. 22, 2021, issued in Korean Patent Application No. 10-2014-0147587.
Chinese Office Action dated Sep. 25, 2019, issued in Chinese Patent Application No. 201510714144.8.
Korean Decision of Grant dated Jun. 16, 2021, issued in Korean Patent Application No. 10-2014-0147587.

* cited by examiner

WEARABLE ELECTRONIC DEVICE

CROSS-REFERENCE TO RELATED APPLICATION(S)

This application is a continuation application of prior application Ser. No. 14/816,535, filed on Aug. 3, 2015, which was based on and claimed priority under 35 U.S.C. § 119(a) to Korean patent application number 10-2014-0147587, filed on Oct. 28, 2014, in the Korean Intellectual Property Office, the disclosure of each of which is incorporated herein by reference in its entirety.

TECHNICAL FIELD

The present disclosure relates to an electronic device. More particularly, the present disclosure relates to an electronic device wearable on, for example, a user's body.

BACKGROUND

An electronic device is a device that performs specific functions according to programs incorporated therein, such as an electronic scheduler, a portable multimedia reproducer, a mobile communication terminal, a tablet PC, an image/sound device, a desktop/laptop computer, a vehicular navigation system, or a home appliance.

For example, such electronic devices may output information stored therein as a sound or an image. As the integration of electronic devices has increased and super high speed and large capacity wireless communication has been popularized, various functions have recently been incorporated in a single mobile communication terminal.

For example, in addition to a communication function, an entertainment function such as a game, a multimedia function, such as music/video image reproduction, a communication and security function for, e.g., mobile banking, and a function of schedule management or electronic wallet, are integrated in a single electronic device.

The electronic devices to be used in a portable manner, such as the electronic scheduler, the portable multimedia reproducer, the mobile communication terminal, and the tablet PC, are generally equipped with a flat display device and a battery, and have a bar-type, folder-type, or sliding-type appearance.

Currently, with the advancement of electronic communication techniques, electronic devices, miniaturized to be wearable on a part of a body, such as a wrist or a head, have become commercially available.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. As wearable electronic devices have become commercially available, interests in healthcare systems have increased. For example, when a wearable electronic device is equipped with a biometric signal sensor, information about a user's health condition may be checked at any time and the checked information may be transmitted as necessary. In using such a wearable electronic device, it is necessary to bring the biometric signal sensor to be in close contact with the user's body when it is desired to check the user's health condition while normally providing a comfortable wearing feeling.

An aspect of the present disclosure is to provide a wearable electronic device that normally provides a comfortable wearing feeling and is capable of precisely detecting a biometric signal, for example, information about the user's health condition.

Another aspect of the present disclosure is to provide a wearable electronic device that presses a biometric signal sensor to be in close contact with the user's body and is easily switched to a comfortable wearing state after the detection of a biometric signal.

In accordance with another aspect of the present disclosure, a wearable electronic device is provided. The wearable electronic device includes a main body, and a wearing unit that allows the main body to be worn on a user's body. The wearing unit may include a first wearing member extending from the main body, a binding member coupled to the first wearing member to be moved in a longitudinal direction of the first wearing member, and a driving member installed in the first wearing member to move the binding member.

In accordance with an aspect of the present disclosure, a method of receiving biometric data from a wearable electronic device is provided. The method comprising tightening, if the wearable electronic device is in a period for acquiring the biometric data, a wearing unit of the wearable electronic device by contracting a binding member coupled to a first wearing member extending from a main body of the wearable device in a longitudinal direction of the first wearing member, acquiring the biometric data via at least one sensor in the main body of the wearable electronic, and outputting, if the acquired biometric data exceeds a threshold, an alarm on the display of the main body of wearable electronic device.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

The same reference numerals are used to represent the same elements throughout the drawings.

DETAILED DESCRIPTION

Figure 1:
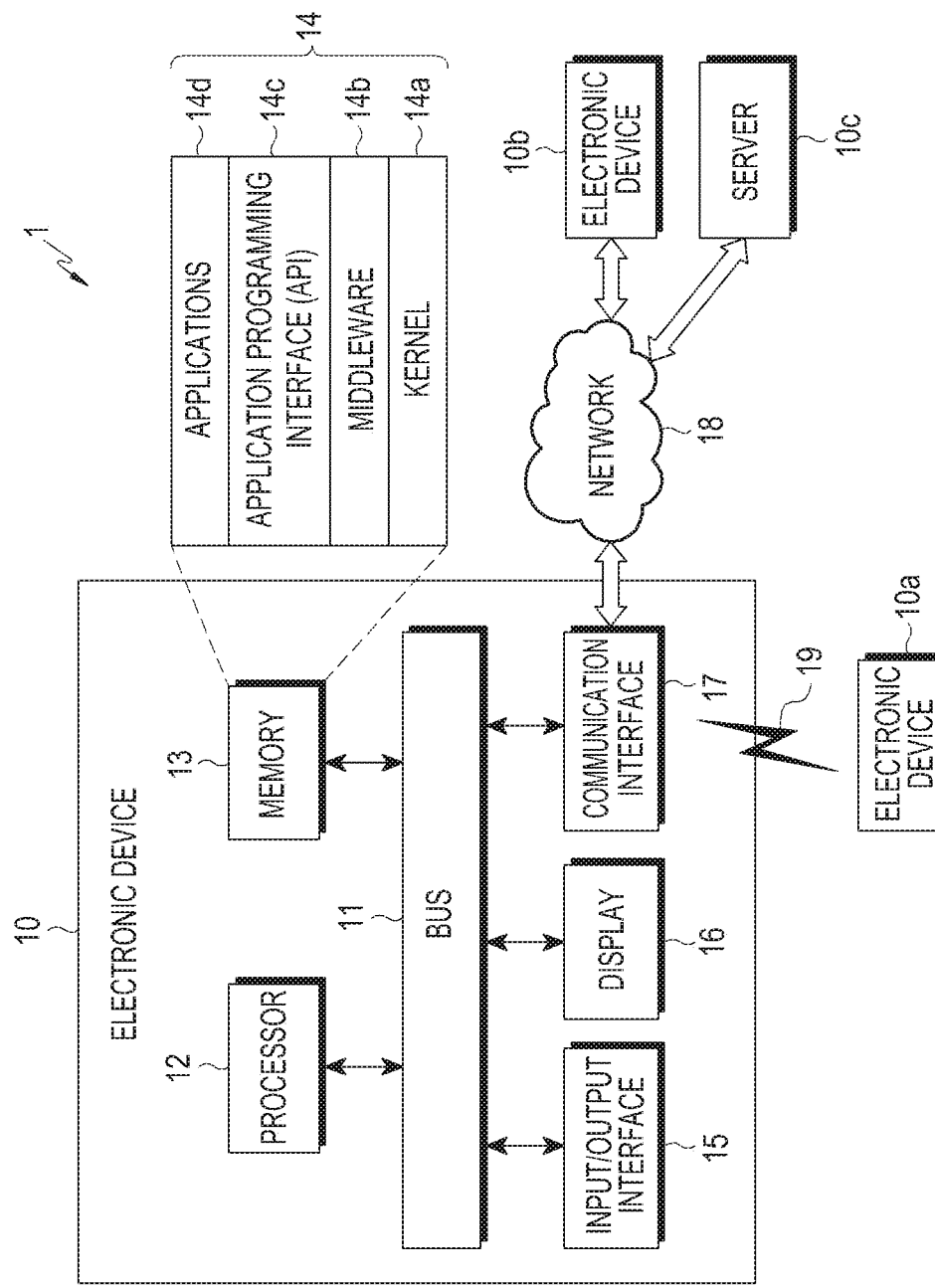
FIG. 1 is a view illustrating a network environment in which a wearable electronic device is operated according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein may be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The present disclosure may have various modifications and embodiments and thus will be described with reference to specific embodiments in detail. However, it should be understood that the present disclosure is not limited to the specific embodiments, but the present disclosure includes all modifications, equivalents, and alternatives within the spirit and the scope of the present disclosure.

Although ordinal terms such as "first" and "second" may be used to describe various elements, these elements are not limited by the terms. The terms are used merely for the purpose to distinguish an element from the other elements. For example, a first element could be termed a second element, and similarly, a second element could be also termed a first element without departing from the scope of the present disclosure. As used herein, the term "and/or" includes any and all combinations of one or more associated items.

Further, the relative terms "a front surface", "a rear surface", "a top surface", "a bottom surface", and the like which are described with respect to the orientation in the drawings may be replaced by ordinal numbers such as first and second. In the ordinal numbers such as first and second, their order are determined in the mentioned order or arbitrarily and may not be arbitrarily changed if necessary.

In the present disclosure, the terms are used to describe a specific embodiment, and are not intended to limit the present disclosure. As used herein, the singular forms are intended to include the plural forms as well, unless the context clearly indicates otherwise. In the description, it should be understood that the terms "include" or "have" indicate existence of a feature, a number, a step, an operation, a structural element, parts, or a combination thereof, and do not previously exclude the existences or probability of addition of one or more another features, numeral, steps, operations, structural elements, parts, or combinations thereof.

Unless defined differently, all terms used herein, which include technical terminologies or scientific terminologies, have the same meaning as that understood by a person skilled in the art to which the present disclosure belongs. Such terms as those defined in a generally used dictionary are to be interpreted to have the meanings equal to the contextual meanings in the relevant field of art, and are not to be interpreted to have ideal or excessively formal meanings unless clearly defined in the present specification.

In the present disclosure, an electronic device may be a random device, and the electronic device may be called a terminal, a portable terminal, a mobile terminal, a communication terminal, a portable communication terminal, a portable mobile terminal, a display device or the like.

For example, the electronic device may be a smartphone, a portable phone, a game player, a TV, a display unit, a heads-up display unit for a vehicle, a notebook computer, a laptop computer, a tablet personal computer (PC), a personal media player (PMP), a personal digital assistants (PDA), and the like. The electronic device may be implemented as a portable communication terminal which has a wireless communication function and a pocket size. Further, the electronic device may be a flexible device or a flexible display device.

The electronic device may communicate with an external electronic device, such as a server or the like, or perform an operation through an interworking with the external electronic device. For example, the electronic device may transmit an image photographed by a camera and/or position information detected by a sensor unit to the server through a network. The network may be a mobile or cellular communication network, a local area network (LAN), a wireless local area network (WLAN), a wide area network (WAN), an internet, a small area network (SAN) or the like, but is not limited thereto.

According to various embodiments of the present disclosure, a wearable electronic device may include a main body and a wearing unit that allows the main body to be worn on a user's body. The wearing unit may include: a first wearing member extending from the main body; a binding member coupled to the first wearing member to be moved in a longitudinal direction of the first wearing member; and a driving member installed in the first wearing member to move the binding member.

In the wearable electronic device as described above, the driving member may be formed of a wire that includes a first end fixed to the main body or the first wearing member and a second end connected to the binding member, and when an electric signal is applied, the wire may be contracted so as to move the binding member in a direction of reducing a length of the wearing unit.

According to an embodiment of the present disclosure, the wearable electronic device may further include an intermediate member that moves the binding member as the wire is contracted. The intermediate member may increase a moving distance of the binding member to be longer than a contracting distance of the wire.

The intermediate member may include at least one link pivotally coupled to the first wearing member. A first point of the link may be connected to the second end of the wire and a second point of the link is connected to the binding member. A pivot axis of the link may be disposed closer to the first point than the second point.

According to an embodiment of the present disclosure, the intermediate member may further include a second link that connects the second point of the link to the binding member.

In accordance with an embodiment of the present disclosure, the first wearing member may include a band that at least partially accommodates the driving member and a fixing plate provided on an end of the band, and the link may be pivotally coupled to the fixing plate.

In the wearable electronic device as described above, the binding member may be movably coupled to the first wearing member in a state where the binding member wraps the fixing plate.

In accordance with an embodiment of the present disclosure, the intermediate member may include at least one pulley disposed on the binding member. The wire may extend via the pulley and the second end of the wire may be fixed to the binding member.

The wearable electronic device as described above may further include a tube fixed in the first wearing member in a zigzag shape or a vortex shape, and the wire may be disposed within the tube.

The wearable electronic device as described above may further include a link assembly having four joint portions formed by coupling four links to be pivotable in relation to each other. The driving member may include a wire that moves first and second joint portions closer to each other, which are arranged in a diagonal direction in relation to each other among the joint portions. The first joint portion may be fixed to the first wearing member and the second joint portion may be fixed to the binding member.

In accordance with an embodiment of the present disclosure, the wire may extend via one of the first and second joint portions so that opposite ends of the wire may be respectively connected adjacent to third and fourth joint portions which are positioned in a diagonal direction in relation to each other among the joint portions. When an electric signal is applied, the wire may be contracted so as to pivot the links in relation to each other.

In the wearable electronic device as described above, the driving member may include a wire made of at least one of an artificial muscle, a shape memory alloy, and an EAP.

An embodiment of the present disclosure, the wearing unit may further include a second wearing member extending from the main body in a direction away from the first wearing member, and the binding member may be bound with the second wearing member so as to keep the wearing unit in a closed curve shape.

An embodiment of the present disclosure, the main body may include a biometric signal sensor disposed on one surface thereof. When the main body is worn on the user's body by the wearing unit, the biometric signal sensor may be positioned to face the user's body.

An embodiment of the present disclosure, the biometric signal sensor may protrude from the surface of the main body.

An embodiment of the present disclosure, biometric signal sensor may detect at least one of blood pressure, electrocardiogram, heart rate variability (HRV), heart rate monitor (HRM), photo plethysmo graph (PPG), sleeping section, skin temperature, heart rate, blood flow, blood sugar, oxygen saturation, pulse wave, and electrocardiogram (ECG).

FIG. 1 is a view illustrating a network environment in which a wearable electronic device is operated according to an embodiment of the present disclosure.

Referring to FIG. 1, descriptions will be made on an electronic device 10 within a network environment 1 in various embodiments. The electronic device 10 may include a bus 11, a processor 12, a memory 13, an input/output interface 15, a display 16, and a communication interface 17.

An implementation of the present disclosure, at least one of the components may be omitted or the electronic device 10 may be additionally provided with another component.

The bus 11 may include a circuit that connects the above-discussed elements 11 to 17 and transmits communicating data (e.g., a control message and/or data) between the elements.

The processor 12 may include one or more of a central processing unit (CPU), an application processor (AP), and a communication processor (CP). The processor 12 may execute, for example, an arithmetic operation or data processing related to a control and/or communication of one or more components of the electronic device 10.

The memory 13 may include a volatile memory and/or a non-volatile memory. The memory 13 may store therein, for example, commands or data related to one or more elements of the electronic device 10.

An embodiment of the present disclosure, the memory 13 may store therein software and/or a program 14. The program 14 may include, for example, a kernel 14a, a middleware 14b, an application programming interface (API) 14c, and/or applications 14d. At least some of the kernel 14a, the middleware 14b, and the API 14c may be referred to as an operating system (OS).

The kernel 14a may control or manage system resources (e.g., the bus 11, the processor 12, or the memory 13) used for executing operations or functions implemented the other programs (e.g., the middleware 14b, the API 14c, or the applications 14d). In addition, the kernel 14a may provide an interface that allows the middleware 14b, the API 14c, or the applications 14d to access individual components of the electronic device 10 so as to control or manage the system recourses.

The middleware 14b may play an intermediary role such that the API 14c or the applications 14d may communicate with the kernel 14a so as to exchange data. In addition, in connection with task requests received from the applications 14d, the middleware 14b may perform a control (e.g., scheduling or load balancing) for the task requests by using, for example, a method of assigning the priority capable of using a system resource of the electronic device 10 (e.g., the bus 11, the processor 12, or the memory 13) to at least one of the applications 14d.

The API 14c is an interface for allowing the applications 14d to control functions provided by the kernel 14a or the middleware 14b and may include, for example, at least one interface or function (e.g., commands) for a file control, a window control, an image processing, or a text control, for example.

The input/output interface 15 may serve as an interface capable of delivering commands or data, entered by a user or an external device to the other component(s) of the electronic device 10. Also, the input/output interface 15 may output commands or data received from the other component(s) of the electronic device 10 to the user or the external device.

The display 16 may include, for example, a liquid crystal display (LCD), a light emitting diode (LED) display, an organic light emitting diode (OLED) display, or a microelectromechanical systems (MEMS) display, or an electronic paper display. The display 16 displays various content (e.g., text, image, video, icon, or symbol) to, for example, the user. The display 16 may include a touch screen, and may receive a touch input, a gesture input, a proximity input or a hovering input using, for example, an electronic pan or a part of the user's body.

The communication interface 17 may set, for example, a communication between the electronic device 10 and an external electronic device (e.g., a first external electronic device 10a, a second external device 10b, or a server 10c). For example, the communication interface 17 may communicate with the external device (e.g., the second external electronic device 10b or the server 10c) by being connected with networks 18 and 19 through a wired or wireless communication.

The wireless communication may use at least one of, for example, long term evolution (LTE), long term evolution advanced (LTE-A), code division multiple access (CDMA), wideband code division multiple access (WCDMA), universal mobile telecommunications system (UMTS), wireless broadband (WiBro) and global system for mobile communications (GSM), as a cellular communication protocol, for example. The wired communication may, for example, universal serial bus (USB), high definition multimedia interface (HDMI), recommended standard 232(RS-232), and POTS (plain old telephone service). The network 18 may include a telecommunication network, for example, at least one of computer network (e.g., LAN or WAN), internet, and telephone network.

Each of the first and second external electronic devices 10a and 10b may be a device that is the same or different type with the electronic device 10.

According to an embodiment of the present disclosure, the server 10c may include a group of one or more servers.

According to various embodiments of the present disclosure, all or some of the operations executed by the electronic device 10 may be executed by one or more other electronic devices (e.g., electronic devices 10a and 10b or the server 10c).

According to an embodiment of the present disclosure, in a case where the electronic device 10 should perform a certain function or service automatically or by a request, the electronic device 10 may request some functions associated therewith from other device (e.g., the electronic devices 10a and 10b or the server 10c) instead of or in addition to executing the function or service by itself. The other electronic devices (e.g., the electronic devices 10a and 10b or the server 10c) may execute the requested functions or additional functions, and transmit the results to the electronic device 10. The electronic device 10 may provide the requested functions or services by processing the received results as they are or additionally. For this purpose, for example, a cloud computing technique, a distributed computing technique, or a client-server computing technique, may be used.

Figure 2:
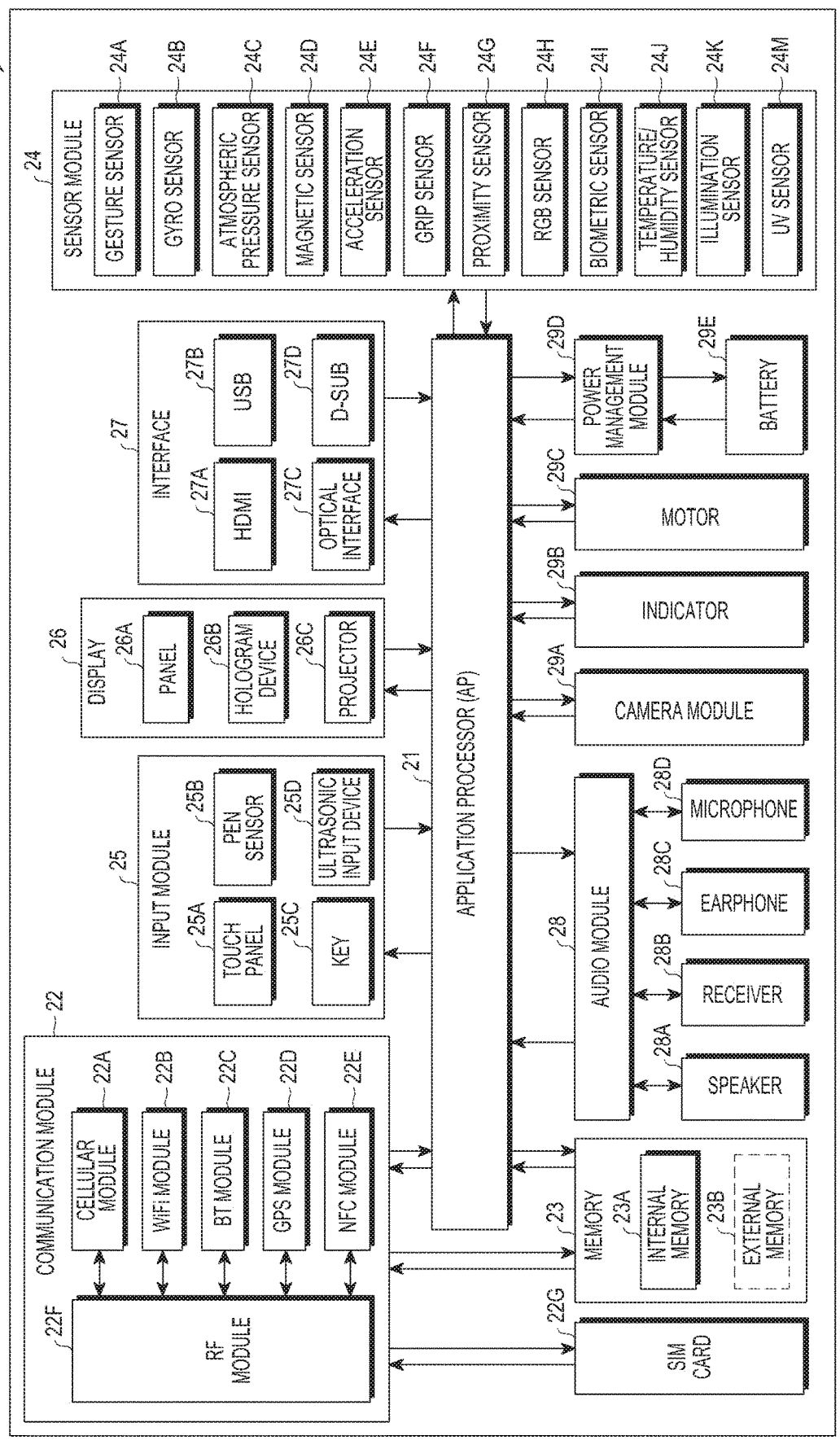
FIG. 2 is a block diagram illustrating an electronic device according to an embodiment of the present disclosure.

FIG. 2 is a block diagram illustrating an electronic device according to various embodiments of the present disclosure.

Referring to FIG. 2, an electronic device 20 may include, for example, the whole or a part of the electronic device 10 illustrated in FIG. 1. The electronic device 20 may include at least one application processor (AP) 21, a communication module 22, a subscriber identification module (SIM) card 22G, a memory 23, a sensor module 24, an input device 25, a display 26, an interface 27, an audio module 28, a camera module 29A, an indicator 29B, a motor 29C, a power management module 29D, and a battery 29E.

The AP 21 may drive, for example, an operating system or applications so as to control a plurality of hardware or software components connected thereto, and may also perform processing and arithmetic operation for various data. The AP 21 may be implemented by a system-on-chip (SoC), for example. According to one embodiment, the AP 21 may further include a graphic processing unit (GPU) and/or an image signal processor. The AP 21 may include at least some of the components illustrated in FIG. 2 (e.g., a cellular module 22A). The AP 21 may load commands or data received from at least one of the other components (e.g., the non-volatile memory) on the volatile memory, process the commands or data, and store various data in the non-volatile memory.

The communication module 22 may have a configuration that is equal or similar to the communication interface 17 of FIG. 1. The communication module 22 may include, for example, the cellular module 22A, a Wi-Fi module 22B, a Bluetooth (BT) module 22C, a global positioning system (GPS) module 22D, a near field communication (NFC) module 22E, and a Radio Frequency (RF) module 22F.

The cellular module 22A may provide, for example, a voice call, a video call, a message service, or an internet service through a communication network.

According to an embodiment of the present disclosure, the cellular module 22A may perform identification and authentication of the electronic device 20 in the communication network, using a subscriber identification module (e.g., the SIM card 22G).

The cellular module 22A may perform at least some of the functions that may be provided by the AP 21.

The cellular module 21A may include a communication processor (CP).

Each of the WiFi module 22B, the BT module 22C, the GPS module 22D, and the NFC module 22E may include, for example, a processor for processing data transmitted/received through a corresponding module.

According to embodiment of the present disclosure, at least some (e.g., two or more) of the cellular module 22A, the WiFi module 22B, the BT module 22C, the GPS module 22D, and the NFC module 22E may be included within a single integrated chip (IC) or IC package.

The RF module 22F may perform data transmission/reception of, e.g., a communication signal (e.g., RF signal). The RF module 22F may include, for example, a transceiver, a power amp module (PAM), a frequency filter, a low noise amplifier (LNA), or an antenna.

According to embodiment of the present disclosure, at least one of the cellular module 22A, the WiFi module 22B, the BT module 22C, the GPS module 22D, and the NFC module 22E may transmit/receive the RF signal through a separate RF module.

The SIM card 22G may include, for example, a card including a subscriber identification module and/or an embedded SIM, and further include unique identification information (e.g., integrated circuit card identifier (ICCID)) or subscriber information (e.g., international mobile subscriber identity (IMSI)).

The memory 23 (e.g., the memory 13) may include an internal memory (23A) or an external memory (23B). The internal memory 23A memory include, for example, at least one of a volatile memory (e.g., dynamic RAM (DRAM), static RAM(SRAM), or synchronous dynamic RAM (SDRAM)), and a non-volatile memory (e.g., one time programmable ROM (OTPROM), programmable ROM (PROM), erasable and programmable ROM (EPROM), Electrically Erasable and Programmable ROM (EEPROM), mask programmed read only memory (mask ROM), flash programmed read only memory (flash ROM), flash memory (e.g., NAND flash or NOR flash), hard drive, or solid state drive (SSD)).

The external memory 23B may further include a flash drive, e.g., compact flash (CF), secure digital (SD), micro secure digital (Micro-SD), Mini Secure Digital (Mini-SD), eXtreme Digital (xD), or memory stick. The external memory 23B may be functionally and/or physically connected to the electronic device 20 through various interfaces.

The sensor module 24 may measure, for example, a physical amount or determine the operating condition of the electronic device 20 and covert the measured or determined information into an electric signal. The sensor module 24 may include, for example, at least one of a gesture sensor 24A, a gyro sensor 24B, an atmospheric pressure sensor 24C, a magnetic sensor 24D, an acceleration sensor 24E, a grip sensor 24F, a proximity sensor 24G, a color sensor 24H (e.g., red, green, blue (RGB) sensor), a biometric sensor 24I, a temperature/humidity sensor 24J, an illumination sensor 24K, and a ultraviolet (UV) sensor 24M. Additionally or alternatively, the sensor module 24 may include, for example, an E-nose sensor, an electromyography (EMG) sensor, an electroencephalogram (EEG) sensor, an electrocardiogram (ECG) sensor, an infrared (IR) sensor, an iris scan sensor, and/or a finger scan sensor. The sensor module 24 may further include a control circuit for controlling one or more sensors incorporated therein.

In an embodiment of the present disclosure, the electronic device 20 may further include a processor configured to control the sensor module 24 as a part of the AP 21 or in addition to the AP 21 so as to control the sensor module 24 while the AP 21 is in a sleep state.

The input device 25 may include, for example, a touch panel 25A, a (digital) pen sensor 25B, a key 25C, or an ultrasonic input device 25D. The touch panel 25A may use at least one of, for example, capacitive type, resistive type, infrared type, and ultrasonic type. Also, the touch panel 25A may further include a control circuit. The touch panel 25A may further include a tactile layer so as to provide a tactile reaction to the user.

The (digital) pen sensor 25B may include, for example, a recognition sheet which is a part of the touch panel or is separate from the touch panel. The key 25C may include, for example, a physical button, an optical key, or a keypad. The ultrasonic input device 25D is capable of identifying data by sensing sound waves with a microphone (e.g., the microphone 28D) in the electronic device 20 through an input tool that generates ultrasonic signals.

The display 26 (e.g., the display 16) may include a panel 26A, a hologram device 26B, or a projector 26C. The panel 26A may include a configuration equal to or similar to the display 16 of FIG. 1. The panel 26A may be implemented to be flexible, transparent, or wearable, for example. The panel 26A may be configured as a single module with the touch panel 25A. The hologram device 26B may show a stereoscopic image in the air using interference of light. The projector 26C may project an image onto a screen by projecting light. The screen may be located inside or outside of the electronic device 20.

According to an embodiment of the present disclosure, the display 26 may further include a control circuit for controlling the panel 26A, the hologram device 26B, or the projector 26C.

The interface 27 may include, for example, a high-definition multimedia interface (HDMI) 27A, a Universal serial bus) 27B, an optical interface 27C, or a d-subminiature (D-sub) 27D. The interface 27 may be included, for example, in the communication interface 17 according to the related art in FIG. 1.

Additionally or alternatively, the interface 27 may include, for example, an Mobile High-definition Link (MHL) interface, an SD card multi-media card (MMC) interface, or an infrared data association IrDA) standard interface.

The audio module 28 may bi-directionally convert, for example, sounds and electric signals. At least some components of the audio module 28 may be included, for example, in the input/output interface 15 according to the related art in FIG. 1. The audio module 28 may process sound information inputted or outputted through, for example, a speaker 28A, a receiver 28B, an earphone 28C, or a microphone 28D.

The camera module 29A is, for example, a device capable of photographing a still image and a moving image.

According to an embodiment of the present disclosure, the camera module 29A may include at least one image sensor (e.g., a front sensor or a rear sensor), a lens, an Image Signal Processor (ISP), or a flash (e.g., LED or xenon lamp).

The power management module 29D may manage, for example, the electric power of the electronic device 20.

According to an embodiment of the present disclosure, the power management module 29D may include, for example, a power management integrated circuit (PMIC), an integrated circuit (charger IC), or a battery or fuel gauge. The PMIC may employ a wired and/or wireless charging type. The wireless charging type may include, for example, a magnetic resonance type, a magnetic induction type, or an electromagnetic type, and further include any additional circuit for wireless charging, such as a coil loop, a resonance circuit, or a rectifier. The battery gauge may measure, for example, the residual amount of the battery 29E and a voltage, current, or temperature in a charging process. The battery 29E may include, for example, a rechargeable battery or a solar battery.

The indicator 29B may indicate a specific status (e.g., a booting status, a message status, or a recharging status) of the electronic device 20 or of a part of the electronic device 20 (e.g., the AP 21). The motor 29C may convert an electric signal into a mechanical vibration, and may generate, for example, a vibration effect or a haptic effect. Although not illustrated, the electronic device 20 may include a processor (e.g., GPU) for supporting a mobile TV. The processor for supporting the mobile TV may process media data that complies with standards of, for example, digital multimedia broadcasting (DMB), digital video broadcasting (DVB), or media flow.

Figure 3:
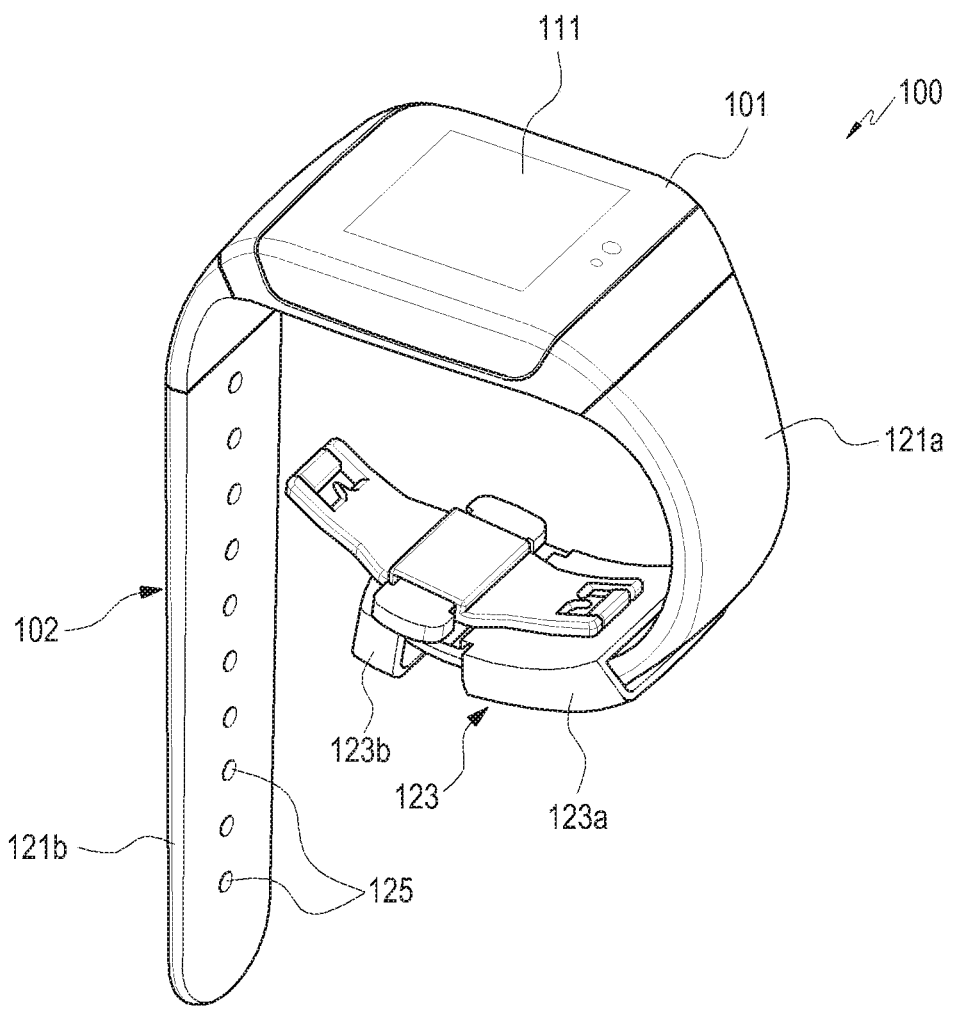
FIG. 3 is a perspective view illustrating a wearable electronic device according to an embodiment of the present disclosure.

FIG. 3 is a perspective view illustrating a wearable electronic device according to various embodiments of the present disclosure.

Figure 4:
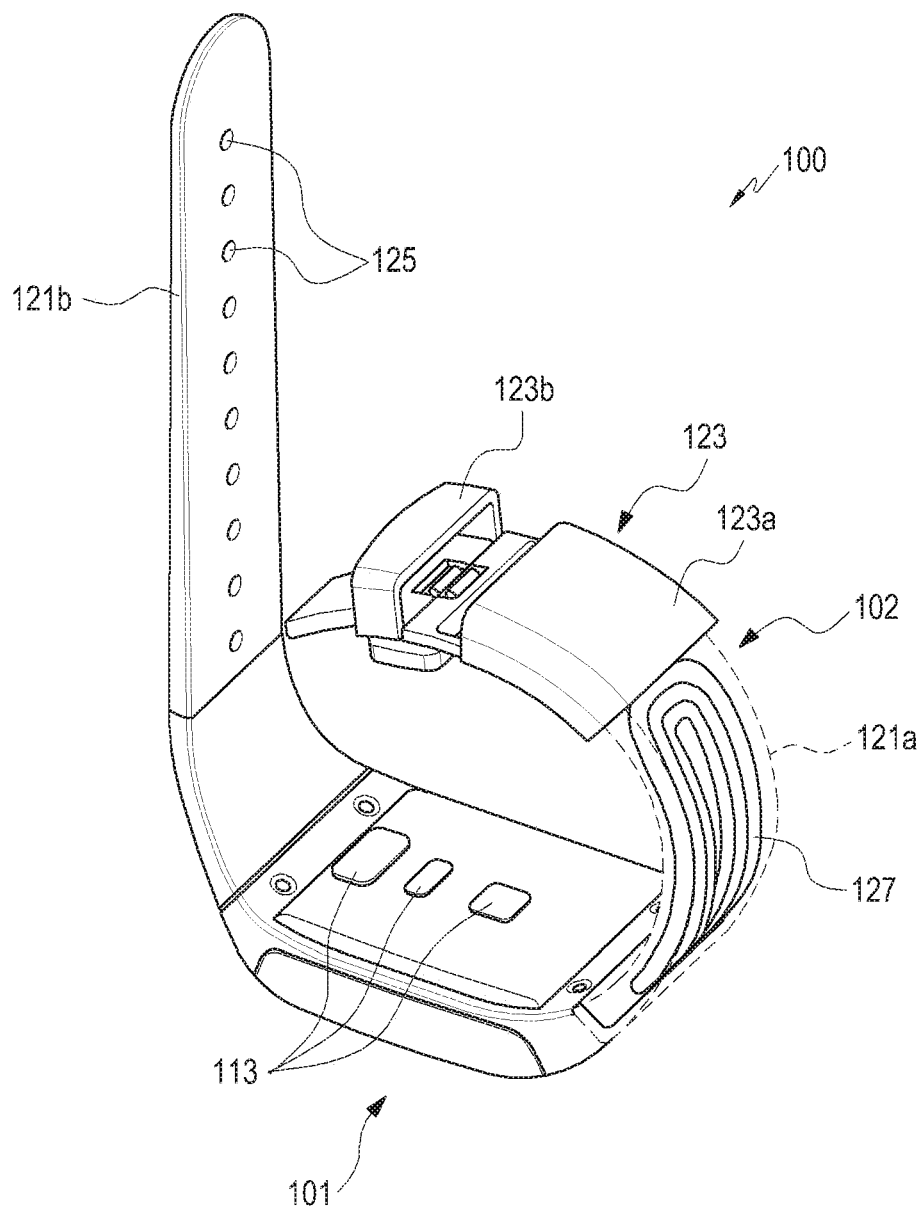
FIG. 4 is a perspective view illustrating a wearable electronic device which is viewed from another direction according to an embodiment of the present disclosure.

FIG. 4 is a perspective view illustrating a wearable electronic device according to various embodiments of the present disclosure which is viewed from another direction according to the related art.

Referring to FIGS. 3 and 4, according to various embodiments of the present disclosure, a wearable electronic device 100 (e.g., the electronic device 10 or 20) includes a main body 101 and a wearing unit 102. The wearing unit 102 may include a first wearing member 121a, a binding member 123, and a driving member 127. The binding member 123 is coupled to the first wearing member 121a and is movable in the longitudinal direction of the first wearing member 121a, and the driving member 127 may move the binding member 123 in a direction where the length of the wearing unit 102 is reduced.

The main body 101 includes various circuit devices, such as an AP, a communication circuit, and a memory device, equipped therein, and a display device 111 mounted on the front surface thereof. On any one surface of the main body 101, for example, on the rear surface, various sensors, for example, biometric signal sensors 113 (e.g., the biometric sensor 24I), and on the front surface (not illustrated), for example, an illumination sensor, may be disposed. The biometric signal sensors 113 are installed to protrude from the rear surface of the main body 101 so that the biometric signal sensors 113 may be more stably in close contact with the user's body. The biometric signal sensors 113 may detect at least one of information items related to the user's health condition, for example, blood pressure, electrocardiogram, HRV, heart rate monitor (HRM), photo plethysmo graph (PPG), sleeping section, skin temperature, heart rate, blood flow, blood sugar, oxygen saturation, pulse wave, and electrocardiogram (ECG).

The wearing unit 102 is provided for allowing the main body 101 to be worn on the user's body, and the first wearing member 121a may extend in one direction from the main body 101. In addition, the wearing unit 102 may further include a second wearing member 121b from the main body 101 in a direction away from the first wearing member 121a. The first and second wearing members 121a and 121b may be implemented as a structure of a band or a watch chain. A binding member 123 may be provided on the first wearing member 121a to be selectively bound to the second wearing member 121b. In the second wearing member 121b, a plurality of binding holes 125 are arranged in the longitudinal direction, and a portion of the binding member 123 is engaged with and bound to at least one of the binding holes 125. The wearing unit 102 maintains a closed curve shape in the state where the binding member 123 is bound with the second wearing member 121b so that the main body 101 may be stably worn on the user's body (e.g., wrist).

The binding member 123 is provided to bind the first wearing member 121a and the second wearing member 121b, in which the binding member 123 may be coupled to the first wearing member 121a to be movable in the longitudinal direction of the first wearing member 121a. As the binding member 123 moves, the length of the wearing unit 102 may be reduced. In the state where the user wears the electronic device 100 (in the state where the binding member 123 binds the first and second wearing members 121a and 121b), when the length of the wearing unit 102 is reduced, the rear surface of the main body 101, for example, the biometric signal sensors 113 may be brought into more close contact with the user's body.

The binding member 123 may include a moving part 123a coupled to at least partially wrap the first wearing member 121a, and a binding part 123b mounted on the moving part 123a to be selectively bound with the second wearing member 121b. The moving part 123a may be installed on an end portion of the first wearing member 121a to be movable in the longitudinal direction of the first wearing member 121a. For example, the end portion of the first wearing member 121a may provide a rail function that guides the movement of the moving part 123a. The binding part 123b may include a protrusion or a pin to be engaged with the binding holes 125, and also provide a holder function that brings a portion of the second wearing member 121b into close contact with the first wearing member 121a.

The driving member 127 may be accommodated in the first wearing member 121a, and may move the binding member 123 in a direction of reducing the length of the wearing unit 102. The driving member 127 may include a wire 127b fabricated using an artificial muscle, a shape memory alloy, an EAP. When the wire 127b is contracted by receiving an electric signal, the binding member 123 may be moved. The structure and arrangement of the driving member 127 will be described in more detail with reference to FIGS. 5 to 8.

Figure 5:
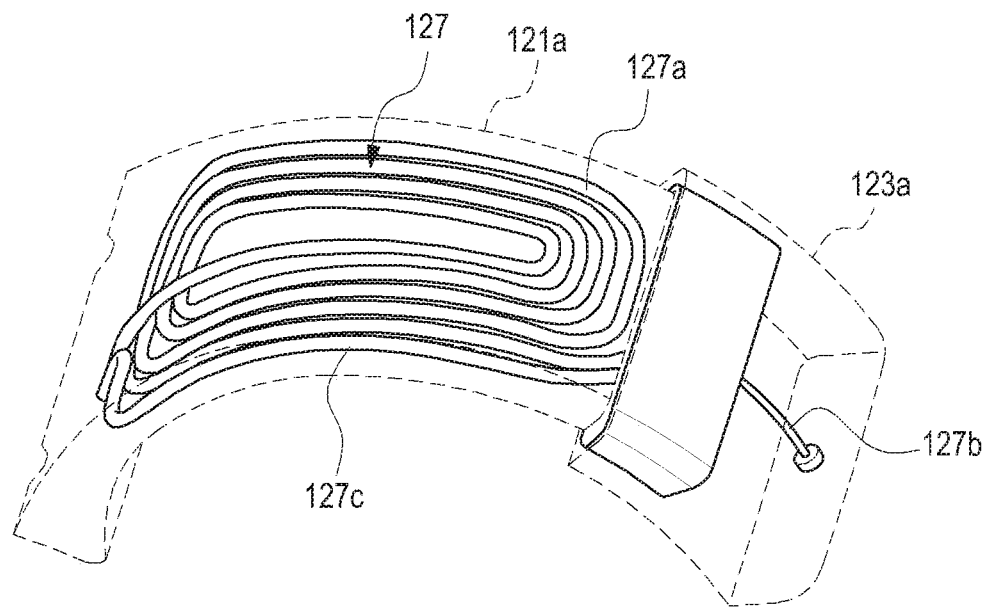
FIG. 5 is a view for illustrating a structure of a wearing unit of a wearable electronic device according to an embodiment of the present disclosure.

FIG. 5 is a view for illustrating a structure of a wearing unit of a wearable electronic device according to one of various embodiments of the present disclosure.

Figure 6:
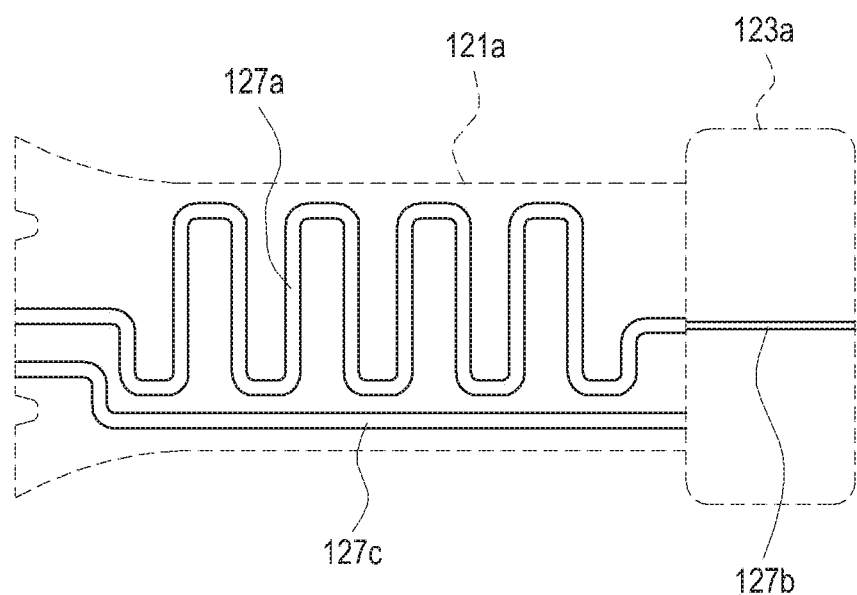
FIG. 6 is a view for illustrating a variation of a structure of a wearing unit of a wearable electronic device according to an embodiment of the present disclosure.

FIG. 6 is a view for illustrating a variation of a structure of the wearing unit of a wearable electronic device according to one of various embodiments of the present disclosure.

Referring to FIGS. 5 and 6, the main body 101 may be brought into close contact with the user's body by reducing the length of the wearing unit 102 as necessary (for detecting a biometric signal) while the wearing unit 102 is worn to be comfortable to the user. When the length of the wearing unit 102 is reduced by about 10 mm, the main body 101 may be brought into close contact with the user's wrist in the state where the electronic device 100 is worn on the wrist such that the user does not feel pressure on the user's body. The wire 127 made of, for example, an artificial muscle, a shape memory alloy, or an EAP may be contracted by about 3 to 5% of the entire length when a driving signal of 9V, 400 mA (3.6 W) is applied thereto although the amount of contraction may slightly differ depending on the material. For example, in the case where the driving member is formed using a wire made of a shape memory alloy and has a length of about 400 mm, a displacement amount of about 12.5 mm in length may be obtained when an electric signal (e.g., a driving signal of 9V, 400 mA (3.6 W)) is applied thereto. For example, the driving member may move the binding member 123 by about 10 mm by using the wire 127b made of the shape memory alloy having a length of 400 mm.

Assuming that the user's wrist is about 200 mm around, it is estimated that the first wearing member 121a is fabricated to have a length of about 100 mm. In order to dispose the wire having a length of about 400 mm in the first wearing member 121a having a length of about 100 mm, the wire 127b may be disposed in a vortex shape according the related art in FIG. 5 or a zigzag shape according to the related art in FIG. 6. The driving member 127, for example, one end of the wire 127b may be fixed to the inside of the main body 101 or the first wearing member 121a, and the other end may be fixed to the binding member 123. A conductive line 127c may be further disposed within the first wearing member 121a in order to apply an electric signal by connecting an electrode to each end of the wire 127b.

The driving member 127 may include a tube 127a. When the wire 127b is contracted in the state where the wire 127b is arranged in the vortex shape or zigzag shape, the diameter of the vortex shape may be reduced or the intervals of the zigzag may be changed. When the arrangement shape of the wire 127b is changed due to the contraction of the wire 127b, the binding member 123 may not be moved by the displacement of the wire 127b. Accordingly, it is possible to suppress the arrangement shape of the wire 127b from being changed by arranging the wire 127b within the tube 127a, and to convert the displacement of the wire 127b into the movement of the binding member 123. Then, the tube 127a may maintain the arrangement shape of the wire 127b while maintaining the flexibility of the first wearing member 121a.

Figure 7:
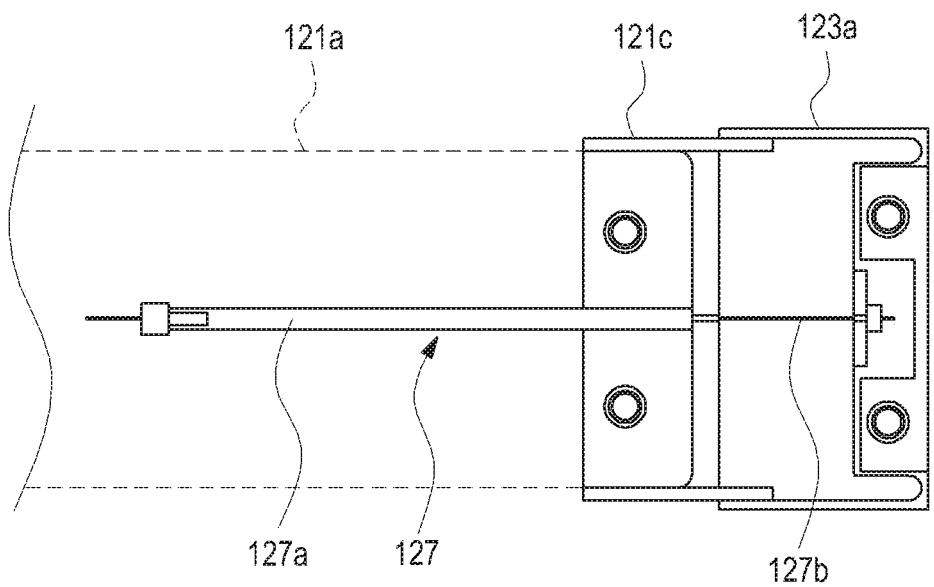
FIG. 7 is a view for illustrating a structure of a driving member of a wearable electronic device according to an embodiment of the present disclosure.

FIG. 7 is a view for illustrating a structure of a driving member of a wearable electronic device according to various embodiments of the present disclosure.

Figure 8:
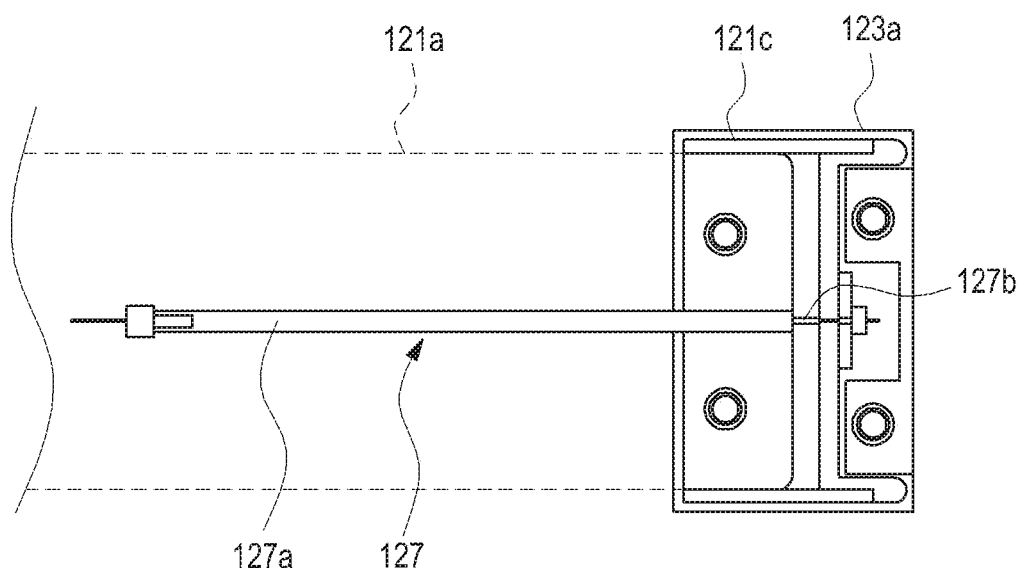
FIG. 8 is a view for illustrating an operating aspect of a driving member of a wearable electronic device according to an embodiment of the present disclosure.

FIG. 8 is a view for illustrating an operating aspect of a driving member of a wearable electronic device according to various embodiments of the present disclosure.

Referring to FIGS. 7 and 8, the first wearing member 121a may include a fixing plate 121c provided at an end thereof. The binding member 123 may move in the longitudinal direction of the first wearing member 121a, for example, in the state where the moving part 123a wraps the fixing plate 121c. The driving member 127, for example, the tube 127a may be fixed to the fixing plate 121c while being arranged within the first wearing member 121a. The wire 127b may further extend to the outside of the fixing plate 121c from the one end of the tube 127a so that the end may be bound and fixed to the binding member 123, for example, the moving part 123a. It is noted that, for example, the conductive line for applying an electric signal to the wire 127b is omitted in FIGS. 7 and 8 for the purpose of concise illustration of the drawings.

When the electric signal is applied to the driving member 127, the wire 127b is contracted to move the binding member 123 in the direction where the fixing plate 121c is further accommodated as illustrated in FIG. 8. As the binding member 123 moves, the length of the wearing unit 102 is gradually reduced, and the main body 101, for example, the biometric signal sensors 113 may come in closer contact with the user's body. When the electric signal applied to the driving member 127 is cut off, the binding member 123 is returned to the position according to the related art in FIG. 6 by the reaction force applied by the user's body, and the wearing unit may be gradually expanded. Although not illustrated, in order to return the binding member 123 to the position according to the related art in FIG. 7, for example, a bias spring may be further arranged.

Meanwhile, even if the tube 127a is made of a material capable of maintaining the flexibility of the first wearing member 121a, it is unavoidable that the flexibility of the first wearing member 121a may be degraded compared with the wearing member in which the tube 127a is not arranged. In addition, when the tube 127a is arranged in the vortex shape or the zigzag shape so that its length is increased, the flexibility of the first wearing member 121a may further degraded.

According to various embodiments of the present disclosure, the electronic device 100 may further include an intermediate member that increase the displacement of the driving member 127, for example, the wire 127b to move the binding member 123. By arranging the intermediate member, the length of the wire 127b provided in the first wearing member 121a, and hence, the length of the tube 127a may be reduced. A structure of the intermediate member will be described with reference to FIGS. 9 to 13.

Figure 9:
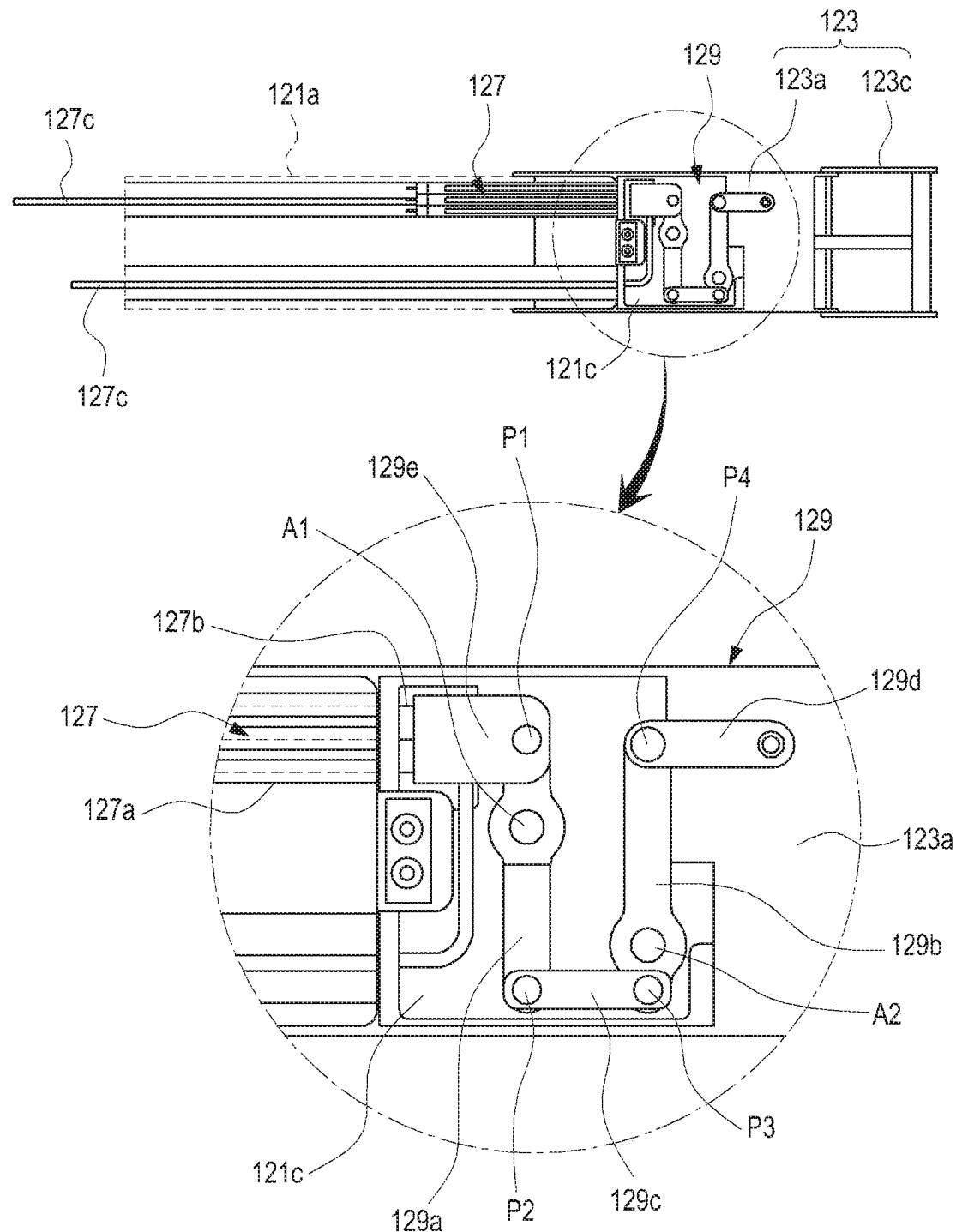
FIG. 9 is a view for illustrating an intermediate member of a wearable electronic device according to an embodiment of the present disclosure.

FIG. 9 is a view for illustrating an intermediate member of the wearable electronic device according to various embodiments of the present disclosure.

Referring to FIG. 9, the wire driving member 127, made of any one of, e.g., an artificial muscle, a shape memory alloy, and an electro-active polymer, may be connected to the binding member 123, for example, the moving part 123a, through an intermediate member 129. The intermediate member 129 is operated by the contraction of the wire 127b, and the binding member 123 may be moved by increasing the displacement of the wire 127b. The wire 127b is arranged within the first wearing member 121a in the state where the wire 127b is accommodated in the tube 127a, and may receive an electric signal applied through the conductive lines 127c. In order to arrange the intermediate member 129, the first wearing member 121a may include a fixing plate 121c provided at an end thereof. The binding member 123 may include a moving part 123a coupled to wrap at least a portion of the first wearing member 121a, for example, the fixing plate 121c, and the moving part 123a may be moved in the longitudinal direction of the first wearing member 121a by being guided by the fixing plate 121c. The binding member 123 may include a binding part 123c having a buckle structure bound with the second wearing member 121b.

The intermediate member 129 may include at least one link. For example, the intermediate member 129 may be implemented as a link assembly. The link may connect the driving member 127, for example, the wire 127b, and the binding member 123 with each other, and increase the displacement of the wire 127b so as to move the binding member 123. The intermediate member 129 may be implemented by a single link.

FIG. 9 further exemplifies a configuration in which each of a pair of links is pivotally coupled to the fixing plate 121c.

One end of the driving member 127, for example, one end of the wire 127b is fixed to the inside of the first wearing member 121a, the other end is connected to a first point P1 of a first link 129a to pivot the first link 129a. A second point P2 of the first link 129a may be connected to the binding member 123 via a second link 129b among the links. In setting the first and second points P1 and P2, the first point P1 may be located closer to the pivot axis A1 of the first link 129a than the second point P2. Through the arrangement of the first and second points P1 and P2 and the pivot axis A1, the displacement of the wire 127b is increased via the first link 129a to pivot or move the second link 129b or the binding member 123. For example, the displacement of the second point P2 according to the pivot of the first link 129a is set to be larger than the displacement of the first point P1. By increasing the distance ratio from the pivot axis A1 of the first link 129a to the first and second points P1 and P2, the moving distance of the binding member 123 in relation to the displacement of the driving member 123 may be further increased.

In the present disclosure, by additionally arranging the second link 129b, the ratio of the moving distance of the binding member 123 in relation to the displacement of the driving member 127 may be further increased. A third point P3 of the second link 129b may be connected to the second point P2 via a first connection link 129c, and the fourth point P4 of the second link 129b may be connected to the binding member 123 via a second connection link 129d. The third point P3 may be located closer to a pivot axis A2 of the second link 129b than a fourth point P4, and the moving distance of the binding member 123 in relation to the displacement of the driving member 127 may be further increased depending on the distance ratio from the pivot axis A2 of the second link 129b to the third and fourth points P3 and P4.

Each of the first and second links 129a and 129b may be arranged in a direction substantially perpendicular to the displacement direction of the driving member 127 or the moving direction of the binding member 123. Through the arrangement of the first and second links 129a and 129b, the displacement of the wire 127b may be more effectively increased. The other end of the driving member 127 may be directly connected to the first point P1. However, in the case where the driving member 127 includes a plurality of wires 127b, the driving member 127 and the first point P1 may be connected with each other by arranging an additional connection link 129e.

When the displacement of the second point P2 is set to about two times the displacement of the first point P1 and the displacement of the fourth point P4 is set to about five times the displacement of the third point P3, the moving distance of the binding member 123 may be increased to ten times the displacement of the wire 127b. For example, in order to contract the wearing unit 102 about 10 mm, a displacement of about 1 mm may be required in the driving member 127. When the wire 127b that forms the driving member 127 has a contraction rate of about 3% when an electric signal (e.g., a driving signal of 9V, 400 mA (3.6 W)) is applied thereto, the driving member 127 may be formed using the wire 127b merely having a length of about 30 mm. However, in consideration of, for example, a manufacturing tolerance or the reaction force of, for example, the first wearing member 121a, the driving member 127 may be formed using the wire 127b having a length of about 40 mm. In this way, a comfortable wearing feeling may be normally provided and the main body 101 may be sufficiently in close contact with the user's body when a biometric signal is measured. In addition, since the length of the driving member 127 is sufficiently reduced, it is possible to alleviate the degradation of the flexibility of the first wearing member 121a due to the arrangement of, for example, the tube.

Figure 10:
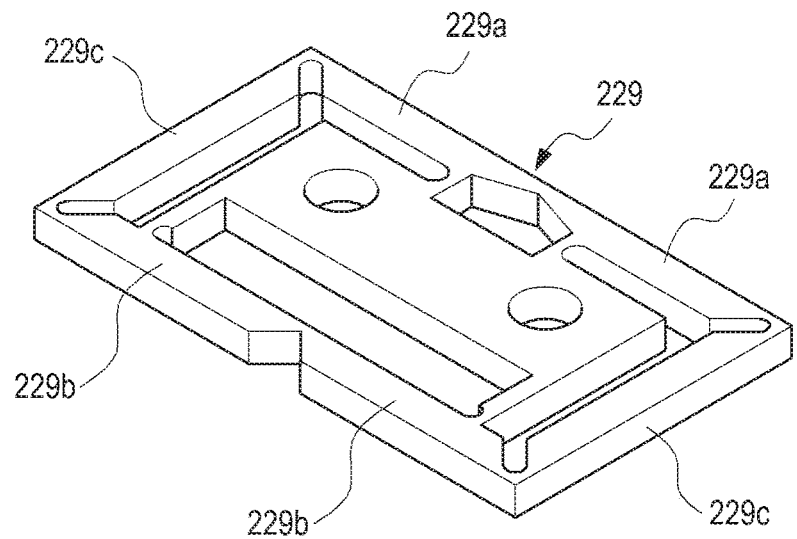
FIG. 10 is a view for illustrating a variation of an intermediate member of a wearable electronic device according to an embodiment of the present disclosure.

FIG. 10 is a view for illustrating a variation of an intermediate member of a wearable electronic device according to various embodiments of the present disclosure.

Figure 11:
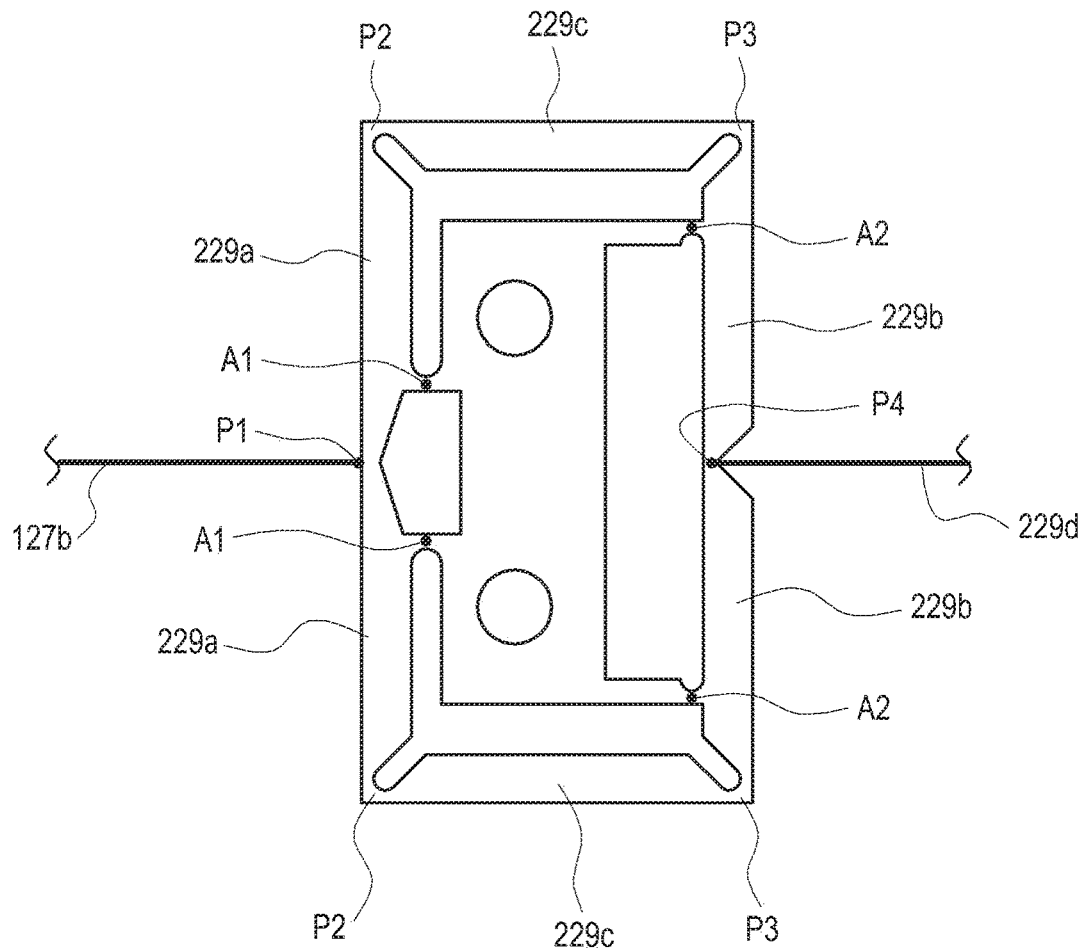
FIG. 11 is a plan view for illustrating a variation of an intermediate member of a wearable electronic device according to an embodiment of the present disclosure.

FIG. 11 is a plan view for illustrating a variation of the intermediate member of a wearable electronic device according to various embodiments of the present disclosure.

Referring to FIGS. 10 and 11, an intermediate member 229 according to the present disclosure is a variation of the link assembly structure of the preceding embodiment. The configuration of the intermediate member 229 will be described, in which the descriptions in the preceding embodiment will be referred to the components similar or equal to those of the preceding embodiment.

The intermediate member 229 may be machined and formed in a rectangular shape. For example, a pair of first links 229a may be arranged on a first side and a pair of second links 229b may be arranged on a second side that is parallel to the first side. On the third and fourth sides of the intermediate member 229, first connection links 229c are arranged so as to link the second points P2 of the first links 229a to the third points P3 of the second links 229b. The first points P1 of the first links 229a may be positioned approximately at the center of the first side of the intermediate member 229 to be in contact with each other and may be connected to the wire 127b of the driving member. The second points P2 of the first links 229a may be respectively connected with the first connection links 229c approximately at the corners where the first side of the intermediate member 229 is connected with the third and fourth sides. The third points P3 of the second links 229b may be respectively connected with the first connection links 229c approximately at the corners where the second side of the intermediate member 229 is connected with the third and fourth sides. The fourth points P4 of the second links 229b are positioned to be in contact with each other approximately at the center of the second side of the intermediate member 229 and may be connected to the binding member through the second connection link 229d. The second connection link 229d may be formed of a rigid wire.

By the contraction of the wire 127b of the driving member, the first and second links 229a and 229b may pivot about the pivot axes A1 and A2, respectively. With the arrangement of the first to fourth points P1, P2, P3, and P4 and the pivot axes A1 and A2, the displacement of the fourth points P4 (e.g., the moving distance of the binding member) in relation to the displacement of the first points P1 (e.g., the displacement of the wire 127b according to the application of an electric signal) may be increased. Apart from this, the moving distance of the binding member in relation to the displacement of the wire may be increased by utilizing various link assembly structures.

Figure 12:
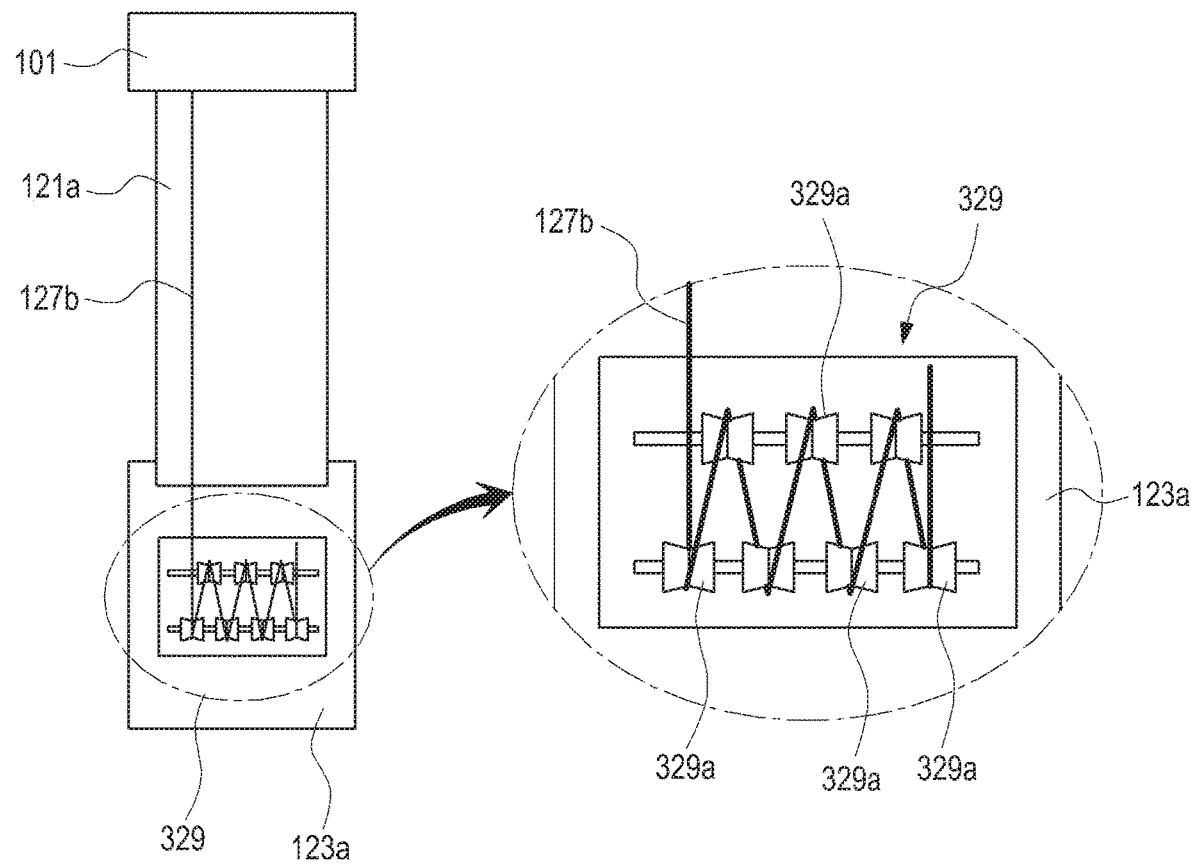
FIG. 12 is a view for illustrating another variation of an intermediate member of a wearable electronic device according to an embodiment of the present disclosure.

FIG. 12 is a view for illustrating another variation of an intermediate member of a wearable electronic device according to various embodiments of the present disclosure.

Referring to FIG. 12. an intermediate member 329 according to the present embodiment may increase the displacement of the binding member, for example, the moving part 123a in relation to the driving member, for example, the wire 127b, using pulleys 329a. The intermediate member 329 may include one or more pulleys 329a mounted on the binding member, for example, the moving part 123a. One end of the wire 127b is fixed to the main body (or the first wearing member), and the other end may be fixed to the moving part 123a and arranged via the pulley 329a. With this arrangement, the moving distance of the moving part 123a may be further increased compared with a real displacement of the wire 127b. For example, in the case where one pulley 329a is arranged, the displacement of the moving part 123a may be increased to two times the real displacement of the wire 127b.

The displacement of the moving part 123a may be increased to four times the real displacement of the wire 127b. For example, in the case where the wire 127b made of a material that is contracted by about 3% of the entire length when an electric signal is applied thereto is used in a length of about 100 mm, and the intermediate member 329 having the pulley structure according to the related art in FIG. 12 is installed, the binding member, for example, the moving part 123a may be moved within a range of about 12 mm.

Figure 13:
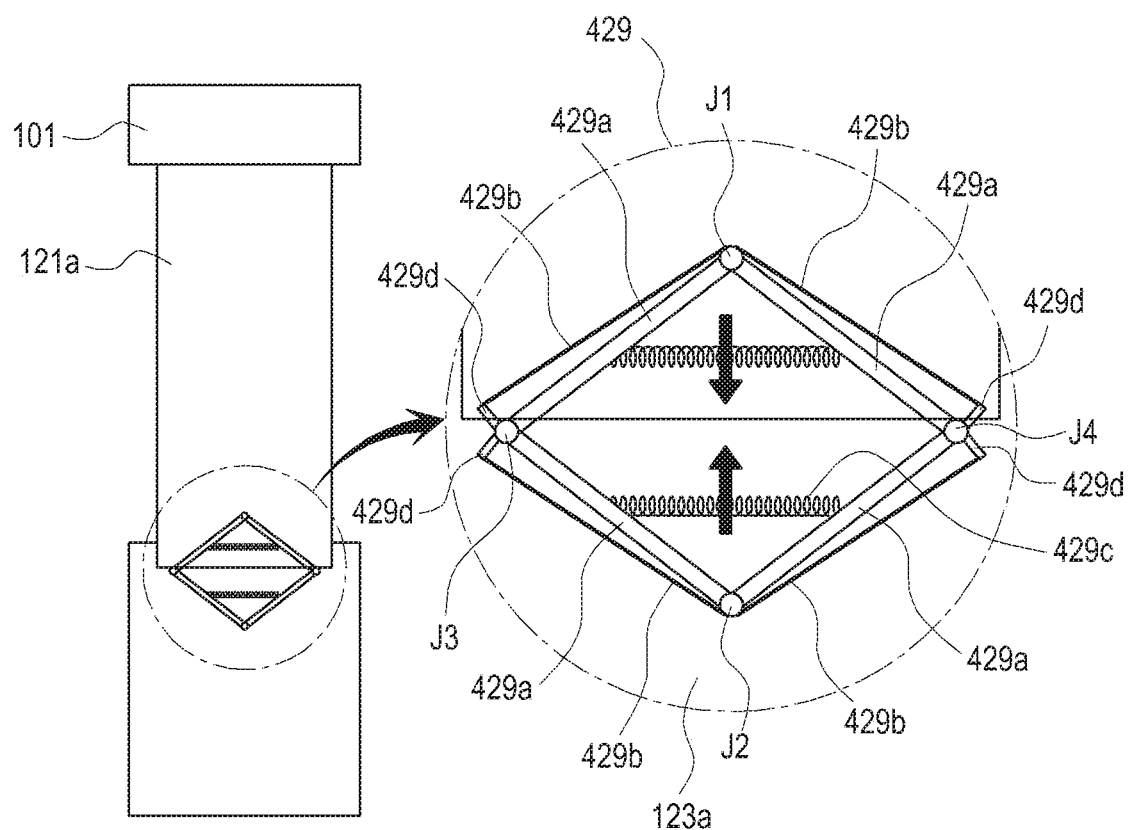
FIG. 13 is a view for illustrating still another variation of an intermediate member of a wearable electronic device according to an embodiment of the present disclosure.

FIG. 13 is a view for illustrating still another variation of an intermediate member of a wearable electronic device according to various embodiments of the present disclosure.

Referring to FIG. 13, an intermediate member 429 according to the present disclosure may have a structure in which a rectangular link assembly is formed with four links 429a, and the diagonal lengths of the link assembly may be adjusted using a driving member, for example, a wire 429b. The links 429a may have the same length and may be coupled to pivot in relation to each other so as to form four joint portions J1, J2, J3, and J4. Among the joint portions, a first joint portion J1 may be fixed to a first wearing member 121a, and a second joint point J2, positioned in the diagonal direction in relation to the first joint portion J1, may be fixed to the moving part 123a of the binding member. For example, the first and second joint portions J1 and J2 may be fixed to the first wearing member 121a and the moving part 123a, respectively, and the links 429a may be pivotally coupled to one of the first and second joint portions J1 and J2.

As the links 429a pivot in relation to each other, a diagonal length of the intermediate member 429, for example, the distance between the first and second joint portions J1 and J2 may be changed to move the moving part 123a in the longitudinal direction of the first wearing member 121a. The wire 429b may be contracted by receiving an electric signal applied thereto, thereby pivoting the links 429a in relation to each other. The wire 429b passes through one of the first and second joint portions J1 and J2, and the opposite ends of the wire 429b may be respectively fixed adjacent to the third and fourth joint portions J3 and J4 which are diagonally positioned in relation to each other. Each of the links 429a may include a driving arm 429d extending from an end positioned at one of the third and fourth joint portions J3 and J4. Each of the opposite ends of the wire 429b may be fixed to one of the driving arms 429d. Each of the links 429a is pivoted about one of the third and fourth joint portions J3 and J4, and the driving force generated by the contraction of the wire 429b may act on a point (e.g., a driving arm 429d) out of each of the pivot centers of the links 429a (e.g., first to fourth joint portions J1, J2, J3, and J4) to pivot each of the links 429a. Depending on the distance between the first and third joint portions J1 and J3 per the distance from the third joint portion J3 (or the fourth joint portion J4) to the point where one end of the wire 429b is fixed, the change of the distance between the first and second joint portions J1 and J2 per the displacement of the wire 429b may be increased. As the distance between the first and second joint portions J1 and J2 is reduced, the moving part 123a may move on the first wearing member 121a so as to reduce the length of the wearing unit. As the length of the wearing unit is reduced, the main body 101 may be further in close contact with the user's body, and the biometric signal sensors mounted on the main body 101 may detect the information related to the user's health condition more precisely.

The intermediate member 429 may further include bias springs 429c. The bias springs 429c may provide a driving force acting in a direction where the spacing between the first and second joint portions J1 and J2 is increased. For example, when an electric signal applied to the wire 429b is cut off, the spacing between the first and second joint portions J1 and J2 may be increased again by the driving force of the bias springs 429c. Accordingly, after the detection of a biometric signal is completed, the user may wear the electronic device comfortably in a state where the user's body is not pressed. Meanwhile, when the electric signal applied to the wire 429b is cut off, the driving force by the wire 429b is released so that the moving part 123a may be returned to its original position by the reaction force applied by the user's body. For example, even if the bias springs 429c are not provided, the spacing between the first and second joint portions J1 and J2 may be increased within a permissible range (in a range where the moving part 123a is not out of the first wearing member 121a) unless the electric signal is applied to the wire 429b.

Figure 14:
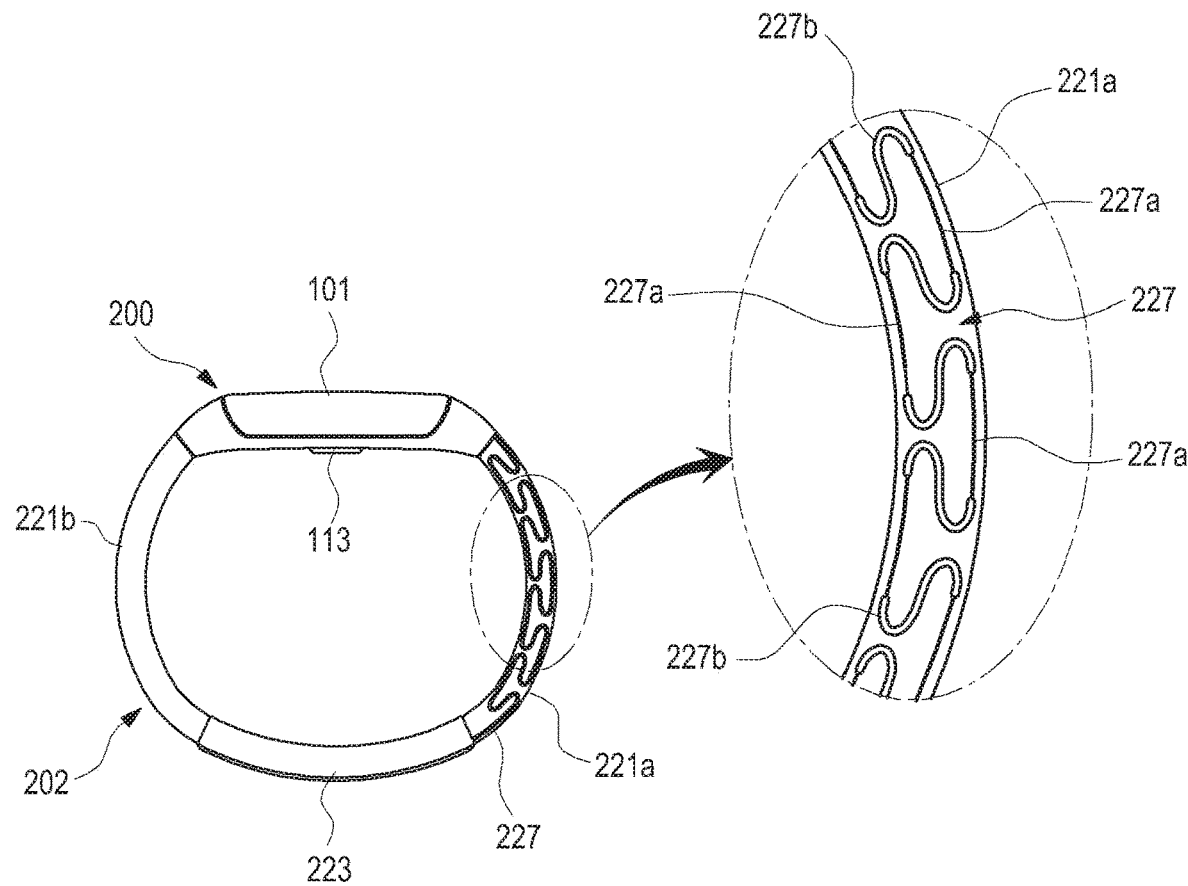
FIG. 14 is a perspective view illustrating a wearable electronic device according to an embodiment of the present disclosure.

FIG. 14 is a perspective view illustrating a wearable electronic device according to various embodiments of the present disclosure.

Referring to FIG. 14, the electronic device 200 according to the present disclosure may include a main body 101 and a wearing unit 202, in which the wearing unit 202 may take a closed curve shape to be worn on the user's body. The wearing unit 202 includes a first wearing member 221a extending from one side of the main body 101, and a second wearing member 221b extending from the other side, in which the first and second wearing members 221a and 221b are bound to each other through a binding member 223 so that the wearing unit 202 may be maintained in the closed curve shape. The binding member 223 may be coupled to an end of the first wearing member 221a to be movable in the longitudinal direction of the first wearing member 221a.

Within the first wearing member 221a, a driving member 227 may be accommodated. The driving member 227 may have a structure in which wires 227a and moving members 227b are alternately connected to each other to form a zigzag form. The wires 227a may be made of any one of an artificial muscle, a shape memory alloy, an electro-active polymer to be contracted when an electric signal is applied thereto. The moving members 227b may be made of a rigid material to be movable in the longitudinal direction of the first wearing member 221a (in a case where the wearing unit 202 has a closed curve shape, in the circumferential direction of the wearing unit 202) within the first wearing member 221a according to the contraction of the wires 227a.

One end of the driving member 227 may be fixed to the main body 101 (or, to the inside of the first wearing member 221a), and the other end may be fixed to the binding member 223. When an electric signal is applied to each of the wires 227a, the wires 227a may move the binding member 223 while being contracted. When the moving members 227b are made of a conductive material, an electrode may be provided at each of the opposite ends of the driving member 227 so as to apply an electric signal to the wires 227a. The moving members 227b are movable in the longitudinal direction of the first wearing member 221a (in a case where the wearing unit 202 has a closed curve shape, in the circumferential direction of the wearing unit 202) within the first wearing member 221a, but the rotation of the moving members 227b within the first wearing member 221a may be restricted. As a result, the driving force generated by the contraction of the wires 227a may move the binding member 223.

While the present disclosure exemplifies a structure in which the other end of the driving member 227 is fixed to the binding member 223, the other end of the driving member 227 may be fixed to the end of the first wearing member 221a if the first wearing member 221a is made of a contractile material. In addition, if the first wearing member 221a is made of a contractile material, the binding member 223 may be fixed to the end of the first wearing member 221a, and the other end of the driving member 227 may be fixed to the binding member 23. In this case, the driving force generated by the contraction of the wires 227a may contract the first wearing member 221a. In addition, if the second wearing member 221b is made of a contractile material, another driving member may also be arranged within the second wearing member 221b.

Figure 15:
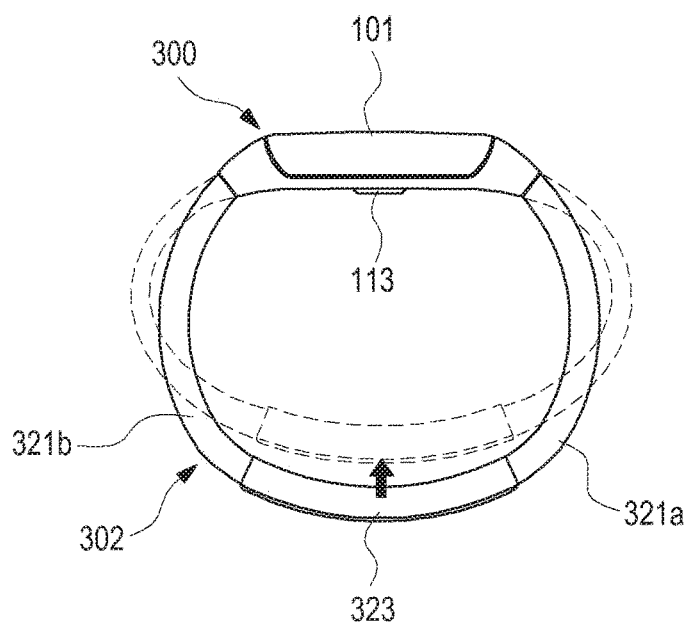
FIG. 15 is a view for illustrating still another variation of a structure of a wearing unit of a wearable electronic device according to an embodiment of the present disclosure.

FIG. 15 is a view for illustrating still another variation of a structure of a wearing unit of a wearable electronic device according to various embodiments of the present disclosure.

Referring to FIG. 15, an electronic device 300 according to the present disclosure may adjust the curvatures of first and second wearing members 321a and 321b that form a wearing unit 302 so as to bring the main body 101 (or the biometric signal sensors 113 mounted on the main body 101) into close contact with the user's body. The first and second wearing members 321a and 321b may be made of a material capable of changing the curvature thereof when an electric signal is applied thereto, such as a shape memory alloy or an electro-active polymer, and the first and second wearing members 321a and 321b may form the driving member by themselves. The first and second wearing members 321a and 321b are in contact with a binding member 323.

According to an embodiment of the present disclosure, if the first and second wearing members 321a and 321b are covered by a material, such as rubber, silicon, or leather, the tactility may be improved when the wearing members are worn. When an electric signal is applied to the first and second wearing members 321a and 321b in the state where the user wears the electronic device 300, the curvature of the first and second wearing members 321a and 321b is reduced so as to press the user's body. As a result, the main body 101 (or the biometric signal sensors 113 mounted on the main body 101) may be further in close contact with the user's body.

According to various embodiments of the present disclosure, the wearable electronic device 100, 200, or 300 includes a driving member made of, for example, an artificial muscle, a shape memory alloy, or an electro-active polymer such that the length or curvature of the wearing unit may be changed. Accordingly, as necessary, the biometric signal sensors mounted on the electronic device may be brought into close contact with the user's body so that information related to the user's health condition may be detected more precisely.

Hereinafter, descriptions will be made on various operating methods of a wearable electronic device according to various embodiments of the present disclosure with reference to FIGS. 16 to 24. In describing the operating methods of the wearable electronic device, reference will be made to the above descriptions for the components or the like of the electronic device.

Figure 16:
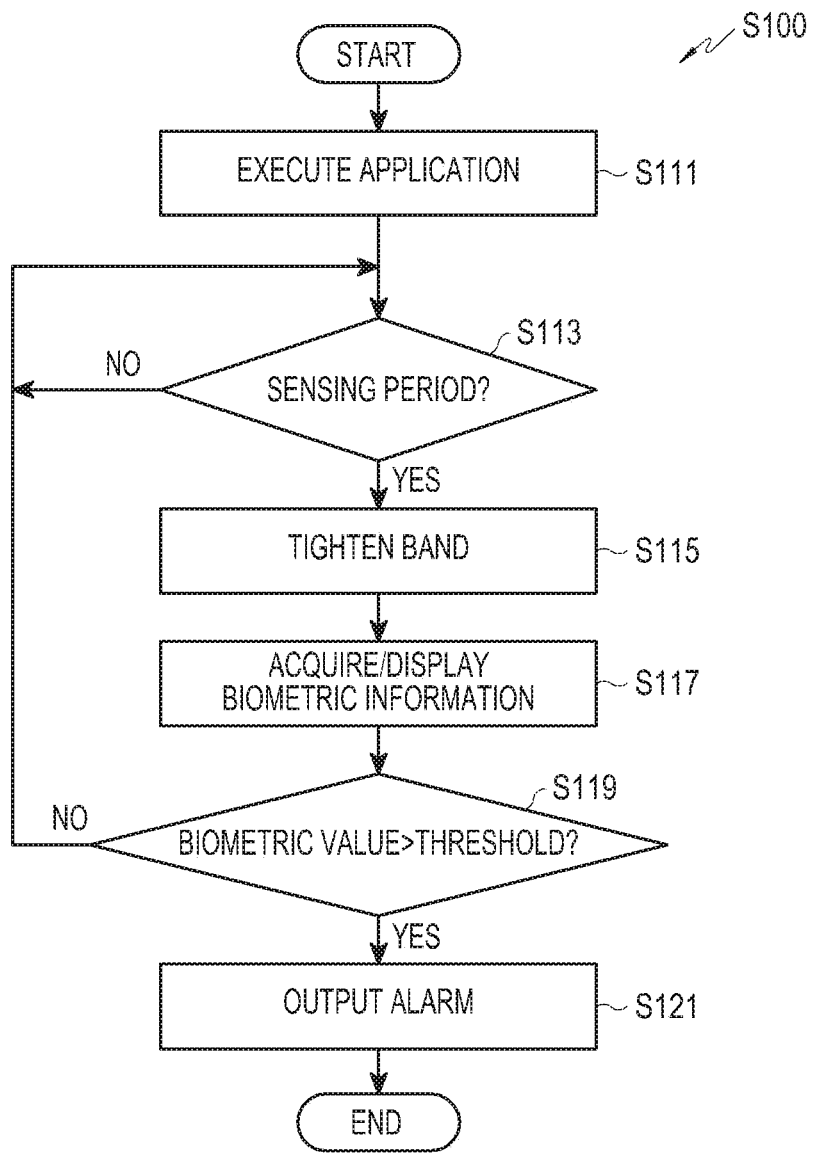
FIG. 16 is a flow chart illustrating one operating method of a wearable electronic device according to an embodiment of the present disclosure.

FIG. 16 is a flow chart illustrating one operating method of a wearable electronic device according to various embodiments of the present disclosure.

Referring to FIG. 16, according to various embodiments of the present disclosure, among methods of operating the wearable electronic device 100, a first method S100 periodically may detect and acquire a user's biometric information and display the acquired biometric information as necessary, or when the value of the detected biometric information exceeds a previously set value or a threshold, may output a warning. When the user's biometric information is periodically acquired, it is possible to check, for example, the change of the user's health condition routinely. Thus, it may be useful for a user who is interested in, for example, health care or a user who requires regular checkups and constant care of, for example, high blood pressure, glycosuria, or cardiac disorder. Here, the user's "biometric information" may include information concerning blood pressure, electrocardiogram, HRV HRM, PPG, sleeping section, skin temperature, heart rate, blood flow, blood sugar, oxygen saturation, pulse wave, or ECG.

Operation S111 for performing the first method S100 is an operation for executing an application for detecting acquiring a biometric signal, in which the application may be executed at regular time intervals according to the setting of the electronic device 100 itself or the user's setting.

According to various embodiments of the present disclosure, the application for detecting and acquiring a biometric signal may be in the state where the application is executed in the background of the electronic device 100.

Subsequently, in operation S113, the electronic device 100 may determine whether the electronic device is in a sensing period. When it is determined that a current period is the sensing period in operation S113, the electronic device 100 performs operation S115 in which the electronic device 100 may drive the driving member 127 so as to gradually reduce the length of the wearing unit 102, for example, the band so that the main body 101 comes in close contact with the user's body (e.g., wrist).

In operation S117, the electronic device 100 may detect and acquire the user's biometric information through the biometric signal sensors 113. As described above, the biometric signal sensors 113 may detect at least one of blood pressure, electrocardiogram, HRV, HRM, PPG, sleeping section, skin temperature, heart rate, blood flow, blood sugar, oxygen saturation, pulse wave, and ECG.

In addition, in operation S117, the acquired user's biometric information may be output through the electronic device 100 or transmitted to or stored in, for example, another electronic device connected with the electronic device 100, a storage medium, or a medical institution capable of being connected with the electronic device 100 through, for example, a communication network. Here, the description, "biometric information may be output" may include outputting the acquired user's biometric information by sound or displaying the acquired user's biometric information on a screen. Since the display device 111 is mounted on the electronic device 100, when the acquired user's biometric information is displayed on the screen, the information needed by the user may be confirmed.

Figure 19:
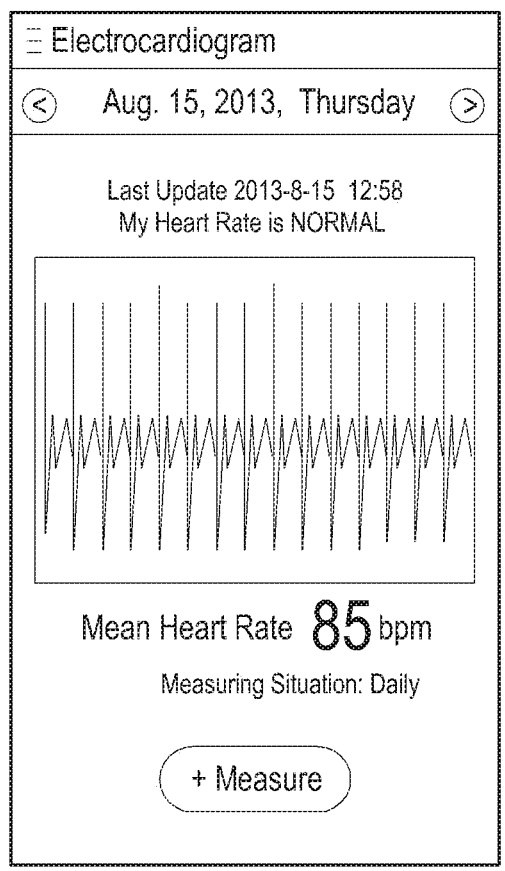
FIGS. 19 to 24 are views illustrating outputting biometric information items measured by operating methods of a wearable electronic device according to an embodiment of the present disclosure.
Figure 20:
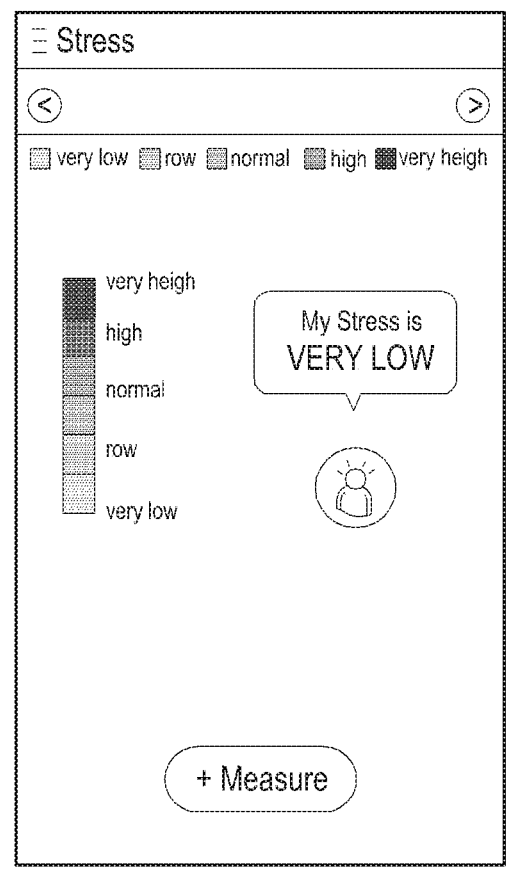
Figure 21:
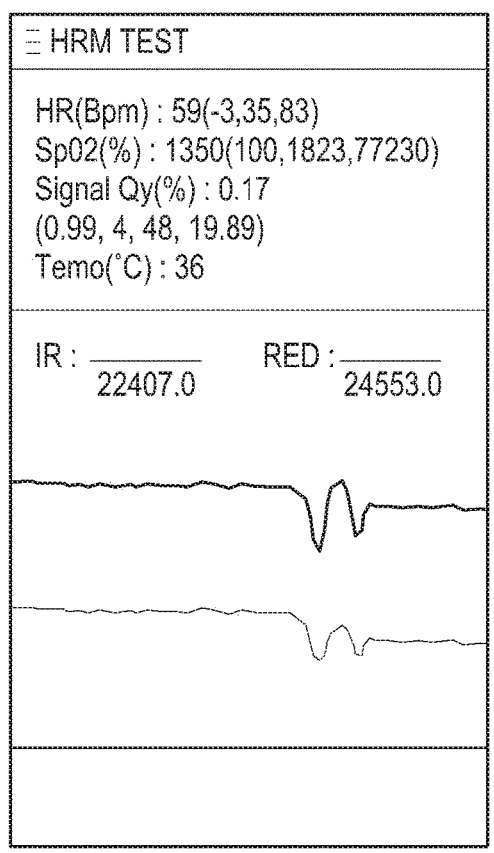

FIGS. 19 to 21 are views illustrating exemplary outputting biometric information items measured by operating methods of a wearable electronic device according to various an embodiments of the present disclosure.

Referring to FIGS. 19 and 20, when information related to, for example, electrocardiogram is detected through the biometric signal sensors 113, the electronic device 100 may output an electrocardiogram waveform and heart rate on a screen. Based on the detected biometric information, for example, blood pressure, electrocardiogram, skin temperature, and oxygen saturation, the electronic device 100 may calculate and output the user's stress index through the display device 111.

Referring to FIG. 21, when the biometric signal sensor 113 detects the user's HRM signal, the electronic device 100 may display the detected information in the combined form of a graph and text on the display device 111.

According to various embodiments, when the electronic device 100 has normally stored information related to the user's health condition, the user's current health condition may be determined by comparing the normally stored information with the detected biometric information. Apart from this, the electronic device 100 may directly output other acquired biometric information on the display device 111, or combine the stored data and the acquired data and provide, for example, a recommendation option for the user's health care to the user, as illustrated in FIGS. 19 and 21.

According to various embodiments of the present disclosure, the first method S100 may further include operation S119 of determining whether the value of the detected biometric information exceeds a pre-set value or a typically recommended threshold. In operation S119, when the value of the detected biometric information is within the threshold, the electronic device 100 may repeatedly perform the above-described operations from operation S111 of determining whether it is the sensing period again.

In operation S119, when the value of the detected biometric information exceeds the threshold, for example, when, for example, a possibility of a heart attack or an abnormal change of blood pressure is determined based on the value of the detected biometric information, the electronic device may output a warning in operation S121. The electronic device 100 may output the warning, for example, by outputting sounds or flickering the screen so as to make the user recognize that the user's health condition is abnormal. In operation S121, the electronic device 100 may output the information related to the user's health condition in various forms, in addition to outputting an acoustic (e.g., sound) or visual (e.g., screen) alarm through the speaker or the display device 111 equipped therein. For example, when it is determined as an emergency situation of, for example, a heart attack through the detected biometric information, the electronic device 100 may transmit an aid request signal including the user's personal information, positional information, and acquired biometric information. The aid request signal may be transmitted to, for example, another electronic device designated by the user of the electronic device 100, another arbitrary electronic device near the electronic device 100, or a medical institute or a first-aid medical center that may be connected via various communication networks.

According to various embodiments of the present disclosure, in the case where both the user of the electronic device that sends, for example, the aid request signal and the user of the electronic device that receives the aid request signal have permitted the transmission/reception of the aid request signal according to the emergency situation, the aid request signal may be transmitted to another arbitrary user's electronic device.

When a series of the operations as described above are completed, the electronic device 100 may releases the tightened state of the wearing unit 102 (e.g., band) so as to provide a comfortable wearing feeling to the user.

According to various embodiments of the present disclosure, based on the acquired user's biometric information, when it is determined that the user's biometric value is in the emergency situation, the electronic device 100 may detect continuously or at more rapid cycles the user's biometric information, and store or transmit the biometric information, to, for example, a medical institute or a first-aid medical center while maintaining the tightened state of the wearing unit 102.

Figure 17:
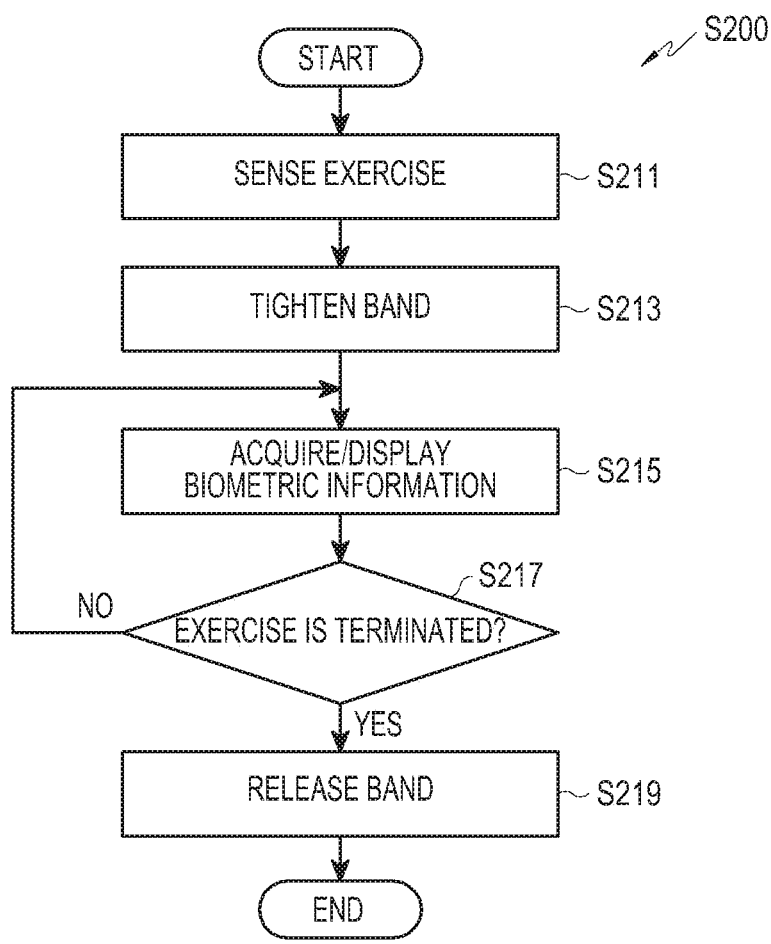
FIG. 17 is a flow chart illustrating another operating method of a wearable electronic device according to an embodiment of the present disclosure.

FIG. 17 is a flow chart illustrating another operating method of a wearable electronic device according to various embodiments of the present disclosure.

Referring to FIG. 17, among methods for operating wearable electronic device 100 according to various embodiments of the present disclosure, the second method S200 is related to calculating, for example, an exercise amount when an unusual sudden change in the user's activity is determined, for example, when the user exercises.

In executing the second method S200, in operation S211, the electronic device 100 may determine whether the user exercises. When the user exercises in the state where the user wears the electronic device 100, a sudden movement of the electronic device 100 may be determined through, for example, a 6-axis sensor. The electronic device 100 may such a sudden movement as an exercise status.

In operation S211, when the exercise status is determined, the electronic device 100 drives the driving member 127 to reduce the length (or curvature) of the wearing unit 102 so that the main body 101 may come in close contact with the user's body in operation S213. As the main body 101 comes in close contact with the user's body, the biometric signal sensors 113 also may come in close contact with the user's body so as to detect a change in the user's biometric information.

In operation S215, while the user is exercising, the electronic device 100 may continuously detect a change in the user's biometric information, such as heart rate and blood pressure, through the biometric signal sensors 113. Based on the detected change in the biometric information, the electronic device 100 may calculate, for example, the user's exercise amount and consumed calories. In addition, the electronic device may quantify and store the user's exercise amount as data by, for example, the user's moving distance and time through, for example, the GPS module. For example, the electronic device 100 may not only calculate the exercise amount from the change in biometric information which is detected by the biometric signal sensors 113, but also acquire information required for calculating the user's exercise amount even through other sensors mounted on the electronic device 100.

In operation S215, for example, the calculated exercise amount may be output as a screen, and may be stored in, for example, a storage medium or any other electronic device or server accessible through a communication network. For example, a personal user may store the exercise amount in the electronic device 100 itself, and may store the exercise amount in, for example, any other storage medium as needed. In the case of a user who requires daily management of, for example, the exercise amount, for example, a sportsman, the calculated exercise amount information or the like may be transmitted to, for example, a manager's electronic device.

Figure 22:
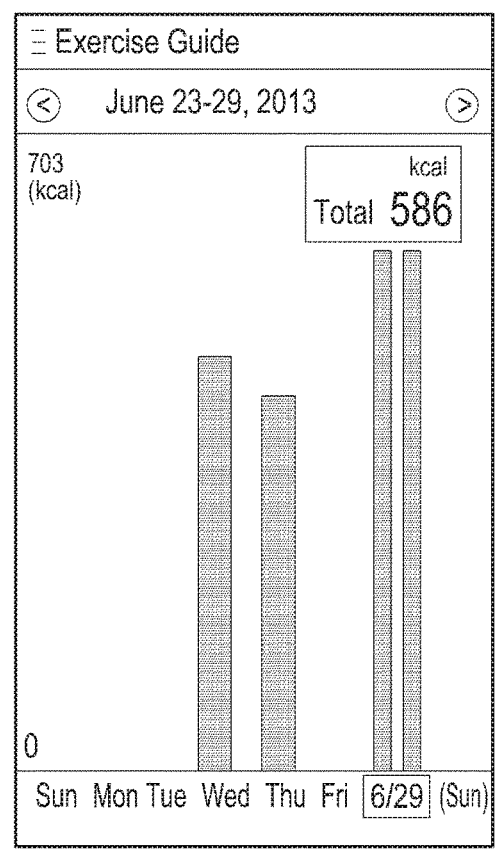

FIG. 22 is a view illustrating exemplary outputting biometric information items measured by operating methods of a wearable electronic device according to various an embodiments of the present disclosure.

Referring to FIG. 22, the electronic device 100 may classify the user's exercise amount information accumulated for a predetermined period by dating (or day of the week) and outputs the user's exercise amount information in the form of a graph through the display device 111. Of course, similarly to the preceding embodiments, for example, the user's exercise amount information may be output in various forms, such as a text form, through the display device 111.

According to various embodiments of the present disclosure, a person who manages a plurality of sportsmen may let each sportsman wear the electronic device 100 while he or she is taking exercise so as to calculate, for example, the exercise amount information. The manager may utilize data prepared by collecting, synthesizing, and analyzing, for example, the calculated exercise amount information by dating and each sportsman so as to plan, for example, future training strategies of each sportsman.

While the above-mentioned process for executing the second method S200 is progressing, or after, for example, the exercise amount information is output, the electronic device 100 may determine whether the user terminates the exercise in operation S217. For example, when the movement of the electronic device 100 determined from, for example, the 6-axis sensor, is slowed down or stopped, the electronic device 100 may recognize that the exercise is terminated and may stop the detection of the biometric information for calculating, for example, the exercise amount.

Operation S219 is an operation for releasing the tightened state of a band, for example, the wearing unit 102 so as to provide a comfortable wearing feeling to the user when the user electronic device 100 recognizes that the exercise is terminated. In operation S219, the electronic device 100 may stop the driving of the driving member 127 to loosen the wearing unit 102, thereby providing the comfortable wearing feeling to the user.

Figure 18:
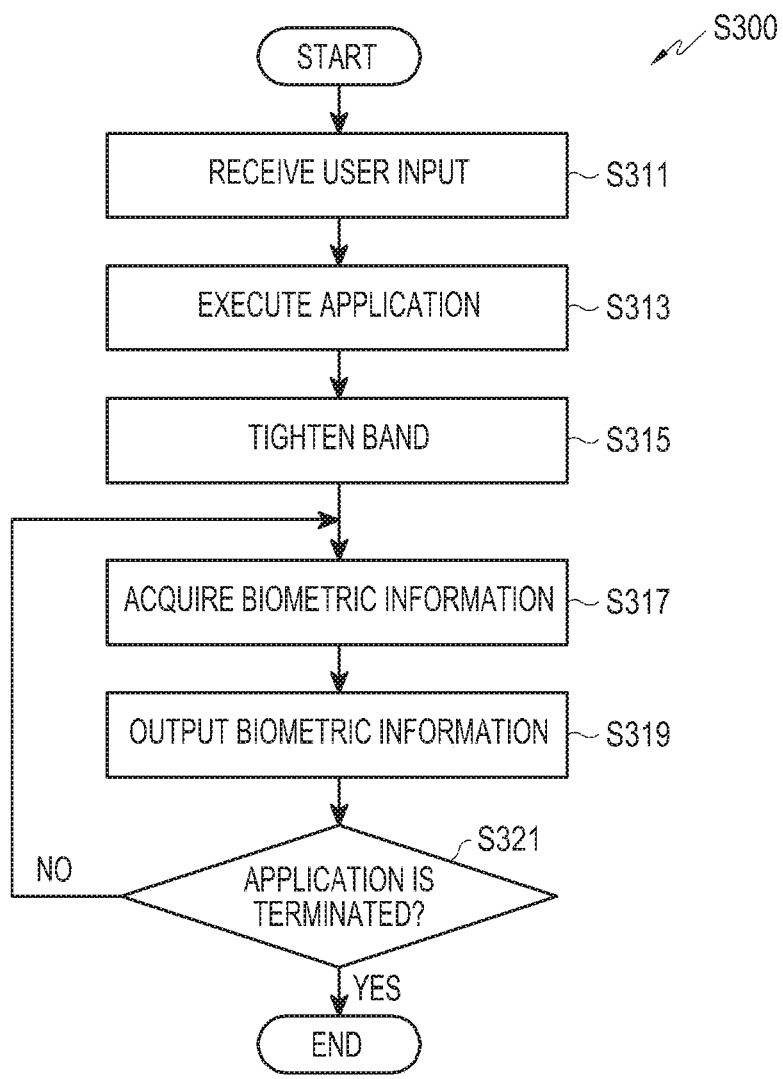
FIG. 18 is a flow chart illustrating still another operating method of a wearable electronic device according to an embodiment of the present disclosure.

FIG. 18 is a flow chart illustrating still another operating method of a wearable electronic device according to various embodiments of the present disclosure.

Referring to FIG. 18, among the methods of operating the electronic device 100, according to the third method S300, the user may operate the electronic device 100 as needed so as to acquire the user's biometric information or biometric information of another person who wears the electronic device 100.

In executing the third method S300, operation S311 is an operation for receiving the user's input. For example, the user may activate an application utilized for acquiring biometric information in the electronic device 100 or may operate, for example, a key provided on the electronic device 100. The electronic device 100 may receive the user's input for obtaining the biometric information from the activation of the application or the key operation.

The electronic device 100 may execute the application corresponding to the user's input in operation S313. The application executed in operation S313 may control a series of processes for acquiring the user's biometric information. For example, in operation S315, the application may make the electronic device 100 drive the driving member 127. As the driving member 127 is driven, the length of a band, for example, the wearing unit 102 is reduced so as to bring the main body 101 into close contact with the user's body.

Operation S317 is an operation for acquiring the user's biometric information. In the state where the main body 101 is in close contact with the user's body, the biometric signal sensors 113 may detect biometric information such as blood pressure and heart rate. The electronic device 100, for example, the executed application may output or separately store the user's detected biometric information in operation S319.

Operation S319 is an operation for outputting (or storing) the detected biometric information. In the case of biometric information that may be detected within a short length of time (e.g., 2 to 5 minutes), the acquired biometric information may be output as a sound or a screen directly after the measurement is complete.

According to various embodiments of the present disclosure, in detection of biometric information that is performed a relatively long length of time (e.g., one hour or more), such as sleeping section and sleeping condition, the information detected for the corresponding length of time is stored in the electronic device 100, and then the corresponding information may be output through the electronic device 100 or transmitted to any other electronic device by the user's direct input.

Figure 23:
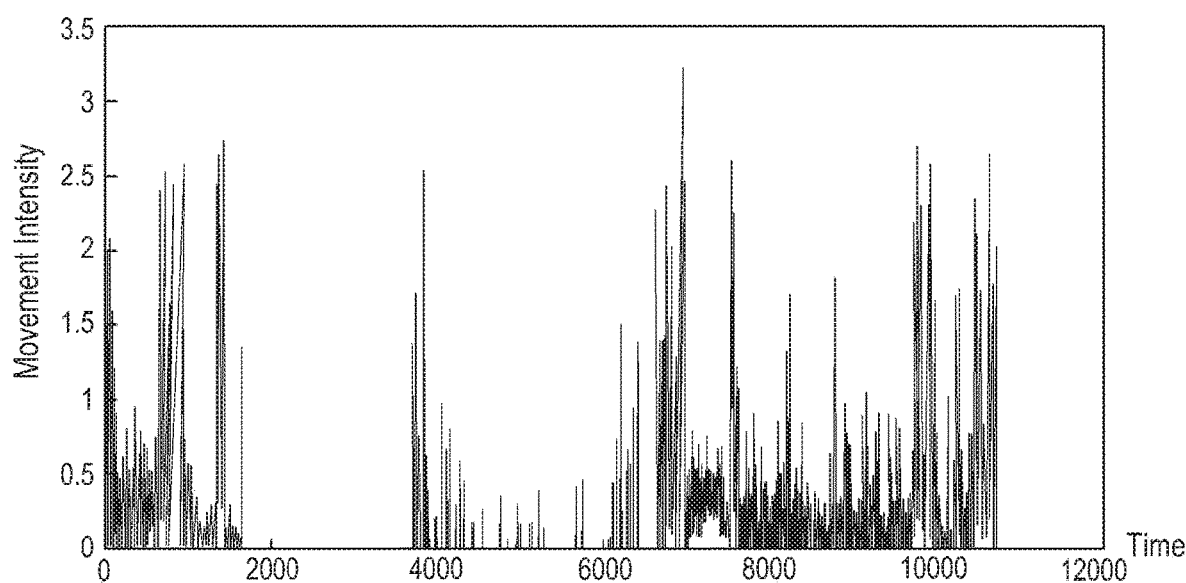

FIG. 23 is a view illustrating exemplary outputting biometric information items measured by operating methods of a wearable electronic device according to various an embodiments of the present disclosure FIG. 23 is a graph output by continuously detecting movement intensity during the user's sleeping section through the electronic device 100. According to various embodiments, it is possible not only to continuously detect and represent the movement intensity during the user's sleeping section as a graph, but also to represent the movement intensity through, for example, other types of diagram. For example, when detecting the user's sleeping section, only a specific section, such as a section where the user sleeps well or a section where the movement intensity is high, may be detected and output as a graph or only the start point and the end point of the corresponding section may be output.

As described above, in the case where the detection of biometric information is performed for a relatively long length of time like the detection of sleeping section, the continuously detected biometric information may be stored in the electronic device 100. According to various embodiments, the detected biometric information may be not only stored in the electronic device 100, but also transmitted to another electronic device, a medical institute, or a first-aid medical center.

When the acquisition and outputting of the user's biometric information are completed, in operation S321, it may be determined whether the executed application is terminated. According to the biometric information desired to acquire, the executed application may be terminated simultaneously when the acquisition and outputting of the biometric information are completed. For example, when the electronic device 100 is in a state where the user has executed the application for detecting a change in, for example, electrocardiogram so as to calculate a stress index, the executed application may be terminated when a predetermined length of time elapses after the calculated stress index is output.

According to various embodiments of the present disclosure, the user may select whether to output the acquired biometric information or whether to terminate the executed application. For example, the biometric information is detected and acquired for a relatively long length of time like the detection of sleeping section, the electronic device 100 may remain in a stand-by state until the user executes a command to output the acquired biometric information, and after the user executes the command to output the acquired biometric information, a screen, on which the user may select whether to terminate the application, may be output.

When the application is terminated according to a setting or by the user's selection, the electronic device 100 may relax the driving member 127 so that the wearing unit 102 may return to its initial state (the state where the user's body is not pressed), thereby providing a comfortable wearing feeling to the user. After the application is terminated, the acquired biometric information may be stored in the electronic device 100, or a storage medium or another electronic device accessible by the electronic device 100 to be utilized as data for the user's continuous health care.

Figure 24:
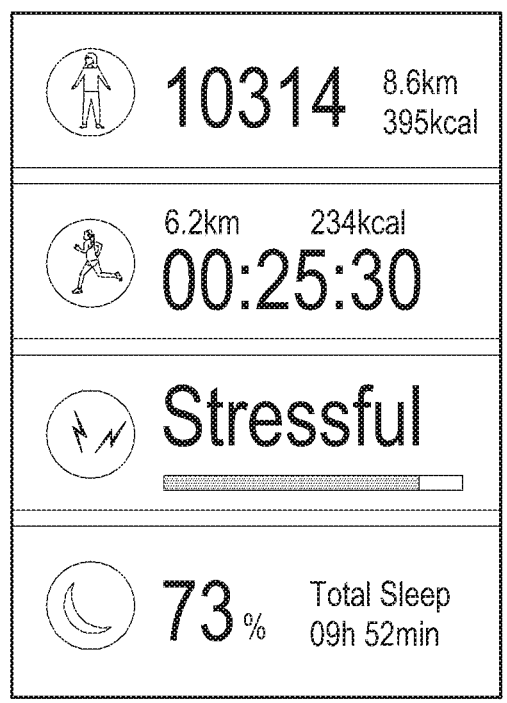

FIG. 24 is a view illustrating one of examples of outputting biometric information measured by a method of operating the wearable electronic device, according to various embodiments of the present disclosure.

Through the electronic device 100, various types of user's biometric information may be acquired. For example, information, such as an exercise amount of, e.g., walking or running, a stress index, and sleeping section, may be acquired, and the electronic device 100 may output the acquired information individually, or output a plurality of pieces of information compositely on one screen as illustrated in FIG. 23. Whether to output individual biometric information or whether to output a plurality of pieces of information may be selected according to the user's selection.

Figure 25:
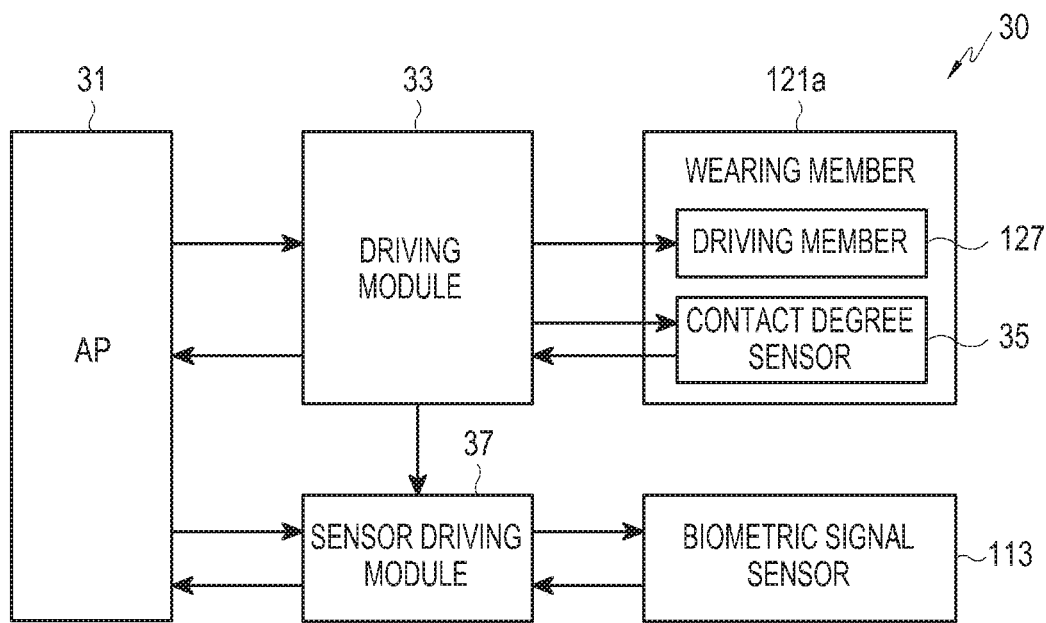
FIG. 25 is a view illustrating a configuration of an operating module implementing a biometric signal sensing operation of a wearable electronic device according to an embodiment of the present disclosure.

FIG. 25 is a view illustrating a configuration of an operating module implementing a biometric signal sensing operation of a wearable electronic device according to various embodiments of the present disclosure.

Figure 26:
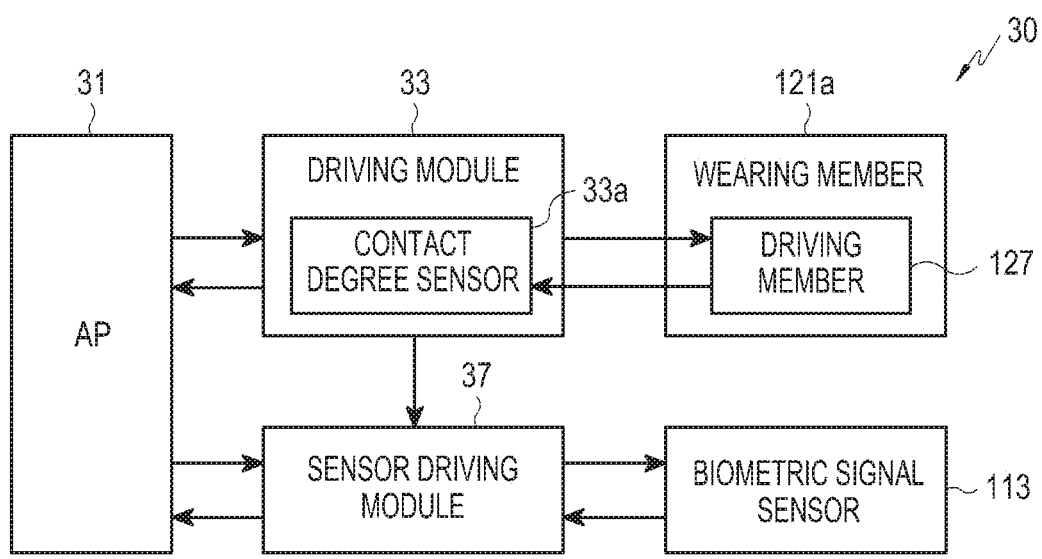
FIG. 26 is a view illustrating a configuration of another operating module implementing a biometric signal sensing operation of a wearable electronic device according to an embodiment of the present disclosure.

FIG. 26 is a view illustrating a configuration of another operating module implementing a biometric signal sensing operation of a wearable electronic device according to various embodiments of the present disclosure.

Referring to FIGS. 25 and 26, the electronic device 100 may include a driving module 33 that adjusts the length of a wearing member, for example, the first wearing member 121a. The driving module 33 may be controlled by a control unit of the electronic device 100 (e.g., an AP 31, a dedicated processor provided in the AP 21 or separately from the AP, or a microprocessor). According to the control of the AP 31, the driving module 33 may operate the driving member 127 mounted on the first wearing member 121a, and according to the operation of the driving member 127, the length of the first wearing member 121a may be adjusted. In the state where the user wears the electronic device 100, the electronic device 100, for example, the main body 101 may come in close contact with the user's body by the operation of the driving member 127.

The electronic device 100 may include a sensor that detects whether the main body 101 is sufficiently in close contact with the user's body, for example, a contact degree sensor 35 or 33a. The contact degree sensor 35 or 33a may be placed on one of the wearing member (e.g., the wearing member 121a) and the driving module 33. In addition, although not illustrated, the contact degree sensor 35 or 33a may be disposed adjacent to the main body 101, for example, the biometric signal sensor 113, or a location where they may be in contact with the user's body, such as the binding member 123.

When the contact degree sensor 35 is provided on the first wearing member 121a, the contact degree sensor 35 may detect the contact degree of the main body (e.g., the main body 101) in relation to the user's body by detecting, for example, the pressure pressing the user's body, and the user's body heat. The contact degree sensor 35 may include an optical sensor. For example, as the main body 101 is in close contact with the user's body, the amount of light detected through the optical sensor may be reduced, which allows the contact degree between the main body and the user's body to be detected.

When the contact degree sensor 33a is provided on the driving module 33, the contact degree sensor 33a may indirectly detect the contact degree between the main body and the user's body. For example, as the contact degree between the main body and the user's body increases, the electric power required for driving the driving member 127 (e.g., current or voltage) or an electric resistance may increase. From this, the contact degree sensor 33a may calculate the contact degree between the main body and the user's body.

The driving module 33 may activate the contact degree sensor 35 or 33a simultaneously with operating the driving member 127, and the contact degree sensor 35 or 33a may detect the contact degree between the main body and the user's body and transmit the detected contact degree to the driving module 33 and the AP 31.

The electronic device 100 may further include a sensor driving module 37 that controls the biometric signal sensor 113, and a sensor driving module 37 may controlled by the AP 31. When it is determined that the main body and the user's body are sufficiently in close contact with each other, the AP 31 or the driving module 33 provides the information to the sensor driving module 37, and the sensor driving module 37 may activate the biometric signal sensor 113. According to an executed application, the activated biometric signal sensor 113 may detect biometric signal information required for the application and provide the detected biometric signal information to the AP 31 through the sensor driving module 37.

The above-described operating methods S100, S200, and S300 of the wearable electronic device may be performed by the operating module 30 as described above. The method of adjusting the length of a wearing unit (e.g., first wearing member 121a) as described above in the above-described operating methods S100, S200, and S300 may be controlled by the driving module 33. Hereinafter, a method of adjusting a length of a wearing unit will be described with reference to FIGS. 27 and 28.

Figure 27:
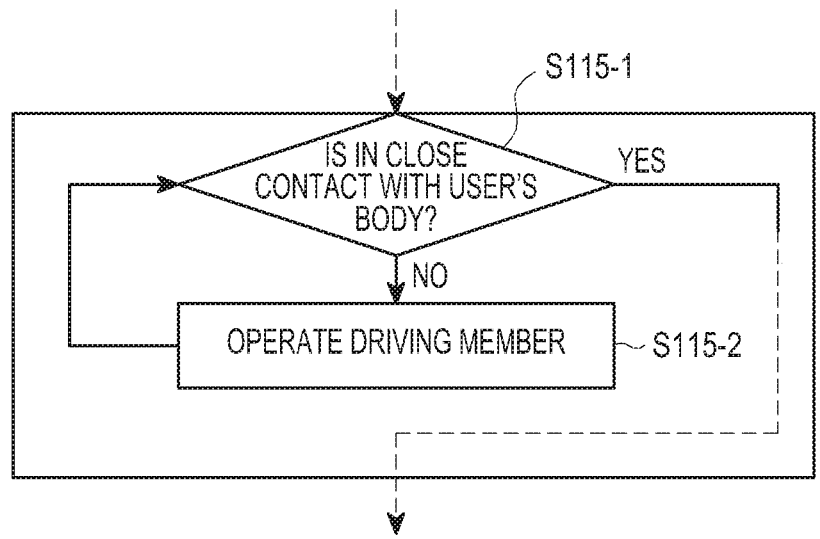
FIG. 27 is a flowchart illustrating a method of adjusting a length of a wearing unit of a wearable electronic device according to an embodiment of the present disclosure.

FIG. 27 is a flowchart illustrating a method of adjusting a length of a wearing unit of a wearable electronic device according to various embodiments of the present disclosure.

Figure 28:
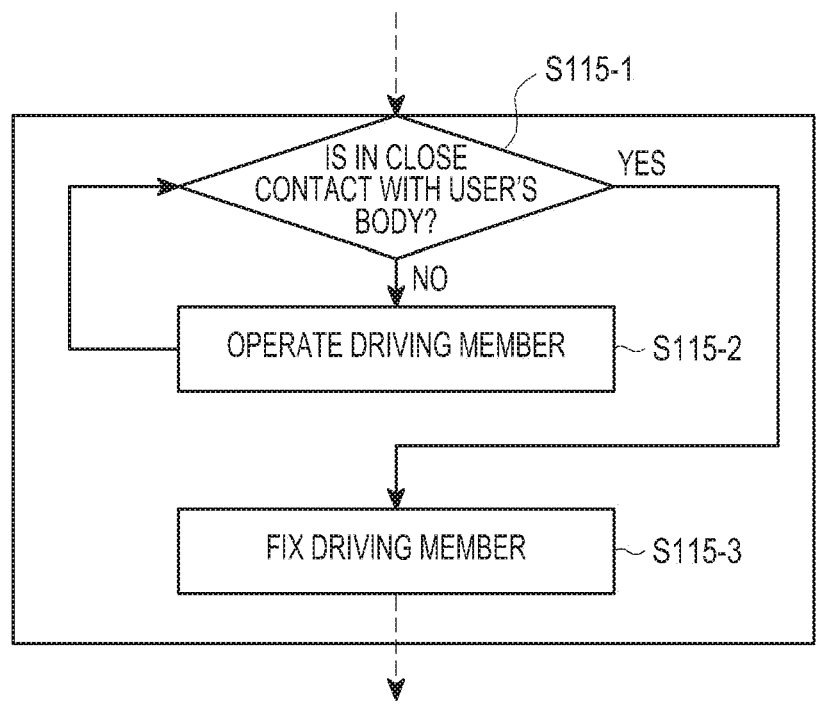
FIG. 28 is a flowchart illustrating another method of adjusting a length of a wearing unit of a wearable electronic device according to an embodiment of the present disclosure.

FIG. 28 is a flowchart illustrating another method of adjusting a length of a wearing unit of a wearable electronic device according to various embodiments of the present disclosure.

Referring to FIGS. 27 and 28, in describing the methods of adjusting a length of a wearing unit 8, reference will be made to operation S115 among operations of tightening a band S115, S213, and S315 as described above. However, it is noted that according to various embodiments of the present disclosure, the method of adjusting a length of a wearing unit is not limited thereto, and operation S213 or operation S315 may also be executed through the methods illustrated in FIGS. 27 and 28 or through various modified methods.

As discussed above with the operating methods S100, S200, and S300, operation S115 may be executed periodically depending on an executed application.

According to various embodiments of the related art, under a predetermined condition, for example, when it is determined that the movement of the user who wears the electronic device becomes active (e.g., sensing excise in operation S211) or an application is executed by the user's input (e.g., operation S313), operation S115 may be performed.

Referring to FIG. 27, for example, an application for detecting a biometric signal is executed, the driving module 33 may be controlled by the AP 31 so as to determine first whether the main body 101 of the electronic device 100 is in close contact with the user's body in operation S115-1. Whether the main body 101 of the electronic device 100 is in close contact with the user's body may be determined based on the data detected from the contact degree sensor 35 or 33a. When the main body 101 is not sufficiently in contact with the user's body, the driving module 33 may operate the driving member 127 in operation S115-2 so as to contract the wearing member (e.g., the first wearing member 121a). The driving module 33 may continuously detect the contact degree between the main body 101 and the user's body while contracting the wearing member so as to maintain or repeat the operation of the driving member 127.

As the wearing member is contracted, the main body 101 gradually comes in close contact with the user's body, and the contact degree sensor 35 or 33a may detect whether the main body 101 and the user's body is brought sufficiently in close contact with each other. Here, "sufficiently in close contact" means that the biometric signal sensors 113 are in close contact with the user's body such that the user's biometric signals may be sufficiently detected, in which the contact degree may be previously set in the process of manufacturing a real product and may be input to and stored in the electronic device 100, for example, the driving module 33. When the main body 101 and the user's body are sufficiently in contact with each other, the driving module 33 may transmit the corresponding information to the AP 31 or the sensor driving module 37.

When the information indicating that the main body 101 and the user's body are sufficiently in close contact with each other is received from the AP 31 or the driving module 33, the sensor driving module 37 may activate the biometric signal sensors 113. For example, the sensor driving module 37 may perform operation S117 and S215 (biometric information acquisition/display) or operation S317 (biometric information acquisition) and operation S319 (biometric information output) of the above-described operating methods S100, S200, and S300.

Referring to FIG. 28, the method of adjusting a length of a wearing unit (e.g., operation S115) may further include an operation of fixing the driving member 127 in operation S115-3. Operation S115-3 is an operation of fixing the driving member 127 when the state, in which the main body 101 is sufficiently in close contact with the user's body, is determined, so that the length of the wearing member (e.g., the first wearing member 121a) may be maintained. For example, in order to maintain the state where the main body 101 is in close contact with the user's body, the electronic device 100 may press the user's body with a predetermined magnitude of force. The driving member 127 may also receive load acting in the direction of extending the length of the wearing member by the force pressing the user's boy. By fixing the driving member 127, operation S115-3 may prevent the length of the wearing member from being extended by the load applied to the driving member 127, and maintain the state where the main body 101 is in close contact with the user's body.

In the state where the fixing member 127 is fixed in operation S115-3 so that the main body 101 is brought into close contact with the user's body, the driving module may transmit the corresponding information to the AP 31 or the sensor driving module 37, and the sensor driving module 37 may activate the biometric signal sensors 113.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A wearable electronic device comprising:
   a main body provided with at least one sensor;
   a processor; and
   a wearing unit that allows the main body to be worn on a user's body,
   wherein the wearing unit comprises:
      a first wearing member extending from the main body,
      a binding member coupled to the first wearing member to be moved in a longitudinal direction of the first wearing member,
      a driving member comprising a wire installed in the first wearing member to move the binding member, and
      an intermediate member configured to, when the wire contracts, move the binding member, wherein the intermediate member comprises a plurality of links connecting the wire with the binding member, the plurality of links being configured to, when the wire contracts, increase a moving distance of the binding member to be longer than a contracting distance of the wire, and
   wherein the processor is configured to:
      execute an application for detecting a user's biometric signal,
      tighten the wearing unit on the user's body, wherein the main body and/or the at least one sensor is configured to come in contact with the user's body when the wearing unit is tightened on the user's body,
      detect the user's biometric signal using the at least one sensor periodically,
      determine whether a user is in an emergency situation based on the detected user's biometric signal, and
      increase a periodicity for detecting the user's biometric signal, in response to determining that the user is in the emergency situation based on the detected user's biometric signal.

2. The wearable electronic device of claim 1, wherein the processor is further configured to:
   release the wearing unit after the detecting of the user's biometric signal.

3. The wearable electronic device of claim 1, wherein the at least one sensor is configured to detect at least one of blood pressure, heart rate variability (HRV), heart rate monitor (HRM), photo plethysmo graph (PPG), sleeping section, skin temperature, heart rate, blood flow, blood sugar, oxygen saturation, pulse wave, and electrocardiogram (ECG).

4. The wearable electronic device of claim 1, wherein the processor is further configured to:
   execute the application at regular time intervals.

5. The wearable electronic device of claim 1, further comprising:
   a memory,
   wherein the processor is further configured to:
      store the detected user's biometric signal in the memory.

6. The wearable electronic device of claim 1, further comprising:
   a display,
   wherein the processor is further configured to:
      output the detected user's biometric signal using the display.

7. The wearable electronic device of claim 1, wherein the processor is further configured to:

transmit the detected user's biometric signal through a communication network.

8. The wearable electronic device of claim 1, wherein the processor is further configured to:
   determine whether a value of the detected user's biometric signal exceeds a pre-set value or a recommended threshold, and
   output an acoustic alarm or a visual alarm when the value of the detected user's biometric signal exceeds the pre-set value or the recommended threshold.

9. The wearable electronic device of claim 8, wherein the processor is further configured to:
   transmit an aid request signal to at least one of an external electronic device, a medical institute or a first-aid medical center through a communication network according to determining that the user is in the emergency situation.

10. The wearable electronic device of claim 9, wherein the aid request signal includes at least one of a user's personal information, a positional information, and the value of the detected user's biometric signal.

11. The wearable electronic device of claim 9, wherein the processor is further configured to:
   detect continuously the user's biometric signal in the emergency situation while maintaining a tightened state of the wearing unit, and
   store the continuously detected user's biometric signal in a memory of the wearable electronic device, or transmit the continuously detected user's biometric signal through the communication network.

12. The wearable electronic device of claim 1, wherein the processor is further configured to:
   determine whether the user exercises using a 6-axis sensor,
   execute the application for detecting a biometric signal when it is determined that the user exercises,
   tighten the wearing unit, and
   detect the user's biometric signal using the at least one sensor.

13. The wearable electronic device of claim 1, wherein the processor is further configured to:
   execute the application for detecting the user's biometric signal based on a user's input.

14. The wearable electronic device of claim 1,
   wherein the processor is further configured to:
      determine whether the wearable electronic device is in a sensing period, and
   wherein the tightening of the wearing unit is performed based on determining that the wearable electronic device is in the sensing period.

15. The wearable electronic device of claim 1, wherein the processor is further configured to:
   tighten the wearing unit by using the driving member to move the binding member in the longitudinal direction of the first wearing member.

16. The wearable electronic device of claim 15, wherein the processor is further configured to:
   release the wearing unit by using the driving member to move the binding member in the longitudinal direction of the first wearing member after the detecting of the user's biometric signal.

17. The wearable electronic device of claim 15, wherein the driving member is made of at least one of an artificial muscle, a shape memory alloy, or an electro-active polymer.

18. The wearable electronic device of claim 15, wherein the processor is further configured to:
   determine whether a value of the detected user's biometric signal exceeds a pre-set value or a recommended threshold, and
   output an acoustic alarm or a visual alarm when the value of the detected user's biometric signal exceeds the pre-set value or the recommended threshold.

19. The wearable electronic device of claim 18, wherein the processor is further configured to:
   determine the emergency situation based on the value of the detected user's biometric signal, and
   transmit an aid request signal to an external electronic device, a medical institute or a first-aid medical center through a communication network according to determining the emergency situation.

* * * * *